US012614615B2

(12) United States Patent
Wang

(10) Patent No.: US 12,614,615 B2
(45) Date of Patent: Apr. 28, 2026

(54) CLINICAL TRIAL SUPPORT APPARATUS, OPERATION METHOD OF CLINICAL TRIAL SUPPORT APPARATUS, AND OPERATION PROGRAM OF CLINICAL TRIAL SUPPORT APPARATUS

(71) Applicant: FUJIFILM CORPORATION, Tokyo (JP)

(72) Inventor: Caihua Wang, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 201 days.

(21) Appl. No.: 18/673,319

(22) Filed: May 24, 2024

(65) Prior Publication Data

US 2024/0312576 A1     Sep. 19, 2024

Related U.S. Application Data

(63) Continuation of application No. PCT/JP2022/040265, filed on Oct. 27, 2022.

(30) Foreign Application Priority Data

Dec. 8, 2021     (JP) ................................. 2021-199612
Jul. 25, 2022     (JP) ................................. 2022-118300

(51) Int. Cl.
*G16H 10/20*                (2018.01)

(52) U.S. Cl.
CPC ................................... *G16H 10/20* (2018.01)

(58) Field of Classification Search
CPC ......... G16H 10/20; G16H 20/10; G16H 70/40
See application file for complete search history.

(56) References Cited

U.S. PATENT DOCUMENTS

| | | | |
|---|---|---|---|
| 2005/0208039 A1 | 9/2005 | Jakobovits et al. | |
| 2010/0280975 A1 | 11/2010 | Wischik et al. | |
| 2014/0249099 A1 | 9/2014 | White et al. | |
| 2016/0367620 A1 | 12/2016 | Demopoulos | |
| 2016/0367621 A1 | 12/2016 | Demopoulos et al. | |

(Continued)

FOREIGN PATENT DOCUMENTS

| | | |
|---|---|---|
| JP | 2007-524361 A | 8/2007 |
| JP | 2016-516007 A | 6/2016 |

(Continued)

OTHER PUBLICATIONS

S. Ostrowitzki et al., "A phase III randomized trial of gantenerumab in prodromal Alzheimer's disease", Alzheimer's Research & Therapy, BioMed Central, UK, 2017.

(Continued)

*Primary Examiner* — Joseph D Burgess
(74) *Attorney, Agent, or Firm* — SOLARIS Intellectual Property Group, PLLC

(57)          ABSTRACT

A clinical trial support apparatus includes a processor, in which the processor predicts a progression speed of a target disease for subjects of a clinical trial, divides the subjects into a plurality of groups according to a prediction result of the progression speed of the target disease, and allocates the subjects to a treatment group to which a test drug is administered and a placebo group to which a placebo is administered for each of the plurality of groups.

10 Claims, 26 Drawing Sheets

(56) References Cited

U.S. PATENT DOCUMENTS

| 2020/0105380 | A1* | 4/2020 | Ennist | G16H 50/70 |
| 2022/0122253 | A1 | 4/2022 | Goto et al. | |
| 2023/0148855 | A1* | 5/2023 | Wang | G06T 7/0016 |
| | | | | 382/128 |

FOREIGN PATENT DOCUMENTS

| JP | 2018-517781 A | 7/2018 |
| WO | 2021/020198 A1 | 2/2021 |

OTHER PUBLICATIONS

International Search Report issued in International Application No. PCT/JP2022/040265 on Dec. 20, 2022.

Written Opinion of the ISA issued in International Application No. PCT/JP2022/040265 on Dec. 20, 2022.

English language translation of the following: Office action dated Mar. 10, 2026 from the JPO in a Japanese patent application No. 2023-566151 corresponding to the instant patent application.

* cited by examiner

Figure 12:
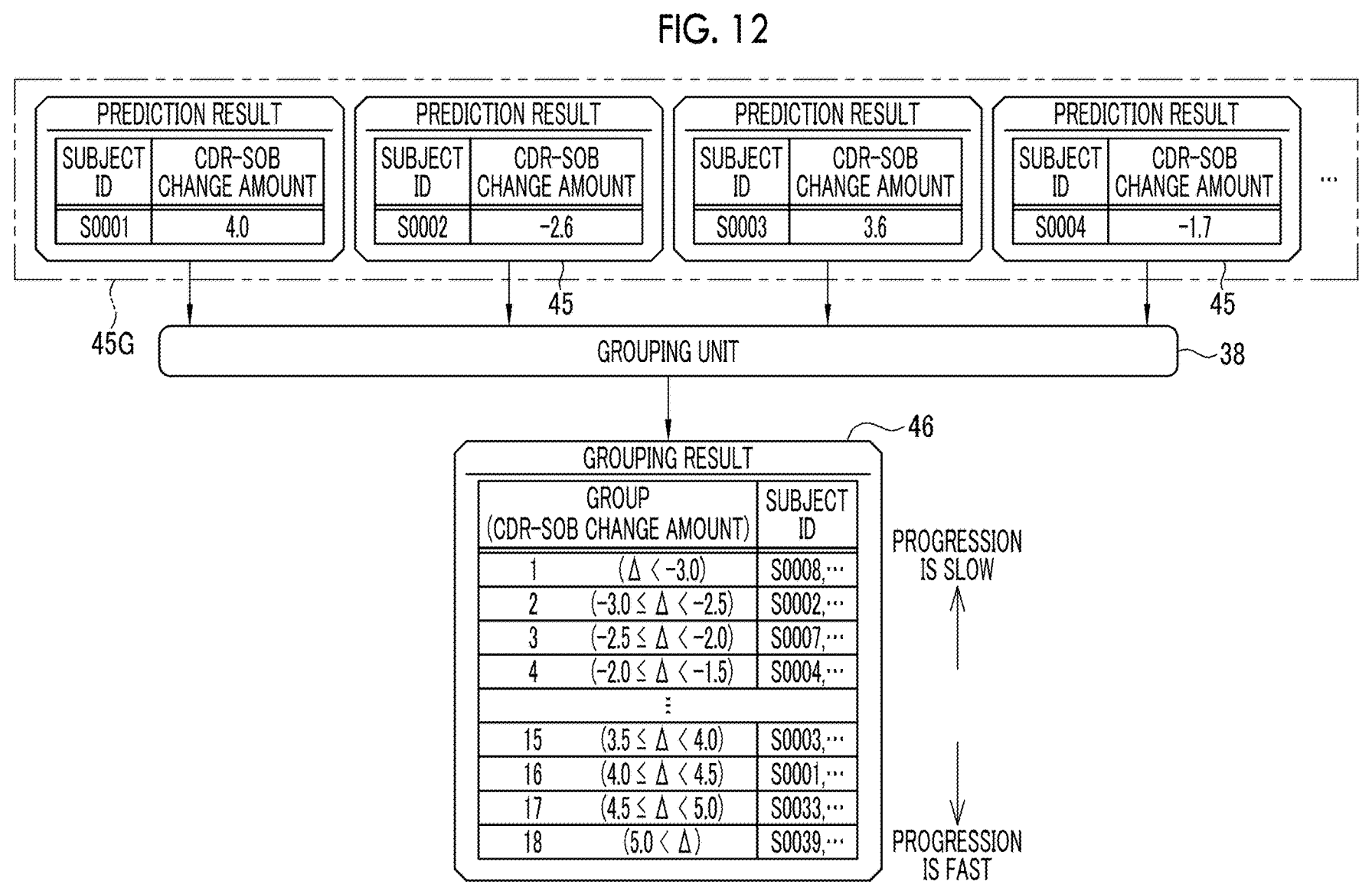

| GROUP (CDR-SOB CHANGE AMOUNT) | | SUBJECT ID |
|---|---|---|
| 1 | (Δ < −3.0) | S0008, ⋯ |
| 2 | (−3.0 ≤ Δ < −2.5) | S0002, ⋯ |
| 3 | (−2.5 ≤ Δ < −2.0) | S0007, ⋯ |
| 4 | (−2.0 ≤ Δ < −1.5) | S0004, ⋯ |
| ⋮ | ⋮ | ⋮ |
| 15 | (3.5 ≤ Δ < 4.0) | S0003, ⋯ |
| 16 | (4.0 ≤ Δ < 4.5) | S0001, ⋯ |
| 17 | (4.5 ≤ Δ < 5.0) | S0033, ⋯ |
| 18 | (5.0 < Δ) | S0039, ⋯ |

| GROUP | ALLOCATION RULE (BLOCK RANDOMIZATION METHOD IN UNITS OF TWO PERSONS) |
|---|---|
| 1 | [TG,PG] [TG,PG] [PG,TG] [TG,PG] [PG,TG] [PG,TG] |
| 2 | [TG,PG] [PG,TG] [PG,TG] [TG,PG] [PG,TG] [PG,TG] |
| 3 | [PG,TG] [TG,PG] [TG,PG] [TG,PG] [PG,TG] [TG,PG] |
| ⋮ | ⋮ |
| 16 | [TG,PG] [TG,PG] [TG,PG] [TG,PG] [PG,TG] [TG,PG] |
| 17 | [PG,TG] [TG,PG] [PG,TG] [PG,TG] [PG,TG] [PG,TG] |
| 18 | [TG,PG] [TG,PG] [PG,TG] [TG,PG] [PG,TG] [PG,TG] |

＊ TG: TREATMENT GROUP, PG: PLACEBO GROUP

PROBABILITY THAT P2 ≥ 0.01 (CLINICAL THIRD-PHASE TRIAL IS NG)
IN STATE IN WHICH P1 < 0.05 (CLINICAL SECOND-PHASE TRIAL IS OK)
(PROBABILITY THAT EFFICACY OF TEST DRUG IS OVERESTIMATED IN CLINICAL SECOND-PHASE TRIAL)

Eff = 0    Eff = 0.05    Eff = 0.1    Eff = 0.15    Eff = 0.2    Eff = 0.25    Eff = 0.3    Eff = 0.35    Eff = 0.4

0.2
0.18
0.16
0.14
0.12
0.1
0.08
0.06
0.04
0.02
0

· · · COMPARATIVE EXAMPLE

· · · STRATIFIED RANDOMIZATION BASED ON PREDICTION RESULT

· · · STRATIFIED RANDOMIZATION BASED ON TRUE VALUE

CLINICAL TRIAL SUPPORT APPARATUS, OPERATION METHOD OF CLINICAL TRIAL SUPPORT APPARATUS, AND OPERATION PROGRAM OF CLINICAL TRIAL SUPPORT APPARATUS

CROSS-REFERENCE TO RELATED APPLICATIONS

This application is a continuation application of International Application No. PCT/JP2022/040265, filed on Oct. 27, 2022, the disclosure of which is incorporated herein by reference in its entirety. Further, this application claims priority from Japanese Patent Applications No. 2021-199612, filed on Dec. 8, 2021, and No. 2022-118300, filed on Jul. 25, 2022, the disclosures of which are incorporated herein by reference in their entireties.

BACKGROUND

1. Technical Field

The technology of the present disclosure relates to a clinical trial support apparatus, an operation method of a clinical trial support apparatus, and an operation program of a clinical trial support apparatus.

2. Description of the Related Art

With the advent of a full-fledged aging society, efforts are being made to develop a drug (hereinafter, may be referred to as an anti-dementia drug) for preventing an onset of diseases, such as dementia represented by Alzheimer's dementia, or delaying progression of dementia. An efficacy of the anti-dementia drug is evaluated through a clinical trial for a certain period. As a subject (also referred to as a test subject) of the clinical trial of the anti-dementia drug, a person whose progression of dementia is relatively fast is preferable. This is because, in a case of a person whose progression of dementia is relatively slow, it is not clear whether the progression is suppressed by the efficacy of the anti-dementia drug or the progression is delayed by a reason specific to the person.

In the clinical trial, a placebo-controlled trial may be performed in which subjects are allocated to a treatment group to which a test drug is administered and a placebo group to which a placebo drug is administered, and the efficacy of the test drug is verified by comparing the treatment group with the placebo group. The clinical trial is conducted in three stages of clinical trials: a clinical first-phase trial (also referred to as a clinical pharmacological trial) targeting a small number of healthy adults, mainly to examine safety of a test drug and its pharmacokinetics; a relatively small-scale clinical second-phase trial (also referred to as an exploratory trial); and a relatively large-scale clinical third-phase trial (also referred to as a confirmatory trial).

In <S. Ostrowitzki, et al: A phase III randomized trial of gantenerumab in prodromal Alzheimer's disease, Alzheimer's Research & Therapy, 2017.>, a clinical trial method of a test drug of an anti-dementia drug using a placebo-controlled trial is disclosed. In <S. Ostrowitzki, et al: A phase III randomized trial of gantenerumab in prodromal Alzheimer's disease, Alzheimer's Research & Therapy, 2017.>, a speed of progression of dementia of the subject is predicted using a regression model after the clinical trial is completed. Then, the subjects are divided into a group in which the progression of the dementia is relatively fast and a group in which the progression of the dementia is relatively slow according to a prediction result, and a change in cognitive ability in the treatment group and a change in cognitive ability in the placebo group are compared with each other for each group.

SUMMARY

In the placebo-controlled trial, in a case where a bias between subjects whose progression of a target disease, which is a target of the trial, is relatively fast, and subjects whose progression of the target disease is relatively slow occurs between the treatment group and the placebo group, the following problem occurs. For example, a case is considered in which, in the clinical second-phase trial, many subjects whose progression of the target disease is relatively slow are allocated to the treatment group, and many subjects whose progression of the target disease is relatively fast are allocated to the placebo group. In this case, even though the efficacy of the test drug is actually bad, the progression of the target disease appears to be suppressed in the treatment group compared to the placebo group, so that the efficacy of the test drug is overestimated. Therefore, even in a case where the clinical third-phase trial is performed on the assumption that the clinical second-phase trial is cleared, a result showing that the efficacy of the test drug is bad may be obtained in practice, and a time and a cost invested in the clinical third-phase trial may be wasted.

On the contrary, a case is considered in which, in the clinical second-phase trial, many subjects whose progression of the target disease is relatively fast are allocated to the treatment group, and many subjects whose progression of the target disease is relatively slow are allocated to the placebo group. In this case, even though the efficacy of the test drug is actually high, the target disease progresses in the treatment group compared to the placebo group, so that the efficacy of the test drug is underestimated. Therefore, even though the efficacy of the test drug is actually high, the clinical second-phase trial cannot be cleared, and the development may be discontinued without transitioning to the clinical third-phase trial.

One embodiment according to the technology of the present disclosure provides a clinical trial support apparatus, an operation method of a clinical trial support apparatus, and an operation program of a clinical trial support apparatus, which can contribute to legitimate evaluation of an efficacy of a test drug for a target disease.

A clinical trial support apparatus of the present disclosure comprises: a processor, in which the processor predicts a progression speed of a target disease for subjects of a clinical trial, divides the subjects into a plurality of groups according to a prediction result of the progression speed of the target disease, and allocates the subjects to a treatment group to which a test drug is administered and a placebo group to which a placebo is administered for each of the plurality of groups.

It is preferable that the processor selects subjects whose progression of the target disease is relatively fast based on the prediction result, and performs grouping according to the prediction result and allocation to the treatment group and the placebo group, only for the selected subjects.

It is preferable that the processor allocates the subjects to the treatment group and the placebo group by using a block randomization method.

It is preferable that the processor predicts the progression speed of the target disease by using a trained model, the trained model is a trained model that has been trained by using a medical image showing an organ of a target disease patient at a first time point as learning input data and a numerical value indicating a degree of progression of the target disease of the target disease patient at a second time point after a lapse of a period equivalent to a clinical trial period from the first time point as correct answer data, and the processor inputs a medical image showing an organ of the subject at a start time point of the clinical trial to the trained model, and outputs a numerical value indicating a degree of progression of the target disease of the subject at an end time point of the clinical trial as the prediction result from the trained model.

It is preferable that, via the trained model, a plurality of anatomical region images, which are images of a plurality of anatomical regions of the organ, are extracted from the medical image at the start time point of the clinical trial, and the anatomical region image is input to a feature amount derivation model prepared for each of the anatomical regions, and a feature amount of the anatomical region is output from the feature amount derivation model.

It is preferable that the learning input data also includes target disease-related data regarding the target disease of the target disease patient at the first time point, and the processor also inputs target disease-related data regarding the target disease of the subject at the start time point of the clinical trial to the trained model.

It is preferable that the target disease is dementia, and the numerical value is a change amount of a score of a cognitive function test or a probability of the target disease.

It is preferable that the target disease is a cranial nerve disease. In addition, it is preferable that the target disease is dementia.

An operation method of a clinical trial support apparatus of the present disclosure comprises: predicting a progression speed of a target disease for subjects of a clinical trial; dividing the subjects into a plurality of groups according to a prediction result of the progression speed of the target disease; and allocating the subjects to a treatment group to which a test drug is administered and a placebo group to which a placebo is administered for each of the plurality of groups.

An operation program of a clinical trial support apparatus of the present disclosure causes a computer to execute: predicting a progression speed of a target disease for subjects of a clinical trial; dividing the subjects into a plurality of groups according to a prediction result of the progression speed of the target disease; and allocating the subjects to a treatment group to which a test drug is administered and a placebo group to which a placebo is administered for each of the plurality of groups.

According to the technology of the present disclosure, it is possible to provide a clinical trial support apparatus, an operation method of a clinical trial support apparatus, and an operation program of a clinical trial support apparatus, which can contribute to legitimate evaluation of an efficacy of a test drug for a target disease.

BRIEF DESCRIPTION OF THE DRAWINGS

Exemplary embodiments according to the technique of the present disclosure will be described in detail based on the following figures, wherein:

FIG. 1 is a diagram showing a flow from a clinical first-phase trial to a clinical second-phase trial;

FIG. 2 is a diagram showing a flow from the clinical second-phase trial to a clinical third-phase trial;

FIG. 12 is a diagram showing processing of a grouping unit;

FIG. 13 is a diagram showing an allocation table;

FIG. 14 is a diagram showing processing of an allocation unit;

FIG. 18 is a graph showing a probability that an efficacy of a test drug is overestimated in the clinical second-phase trial;

DETAILED DESCRIPTION

First Embodiment

Figure 1:
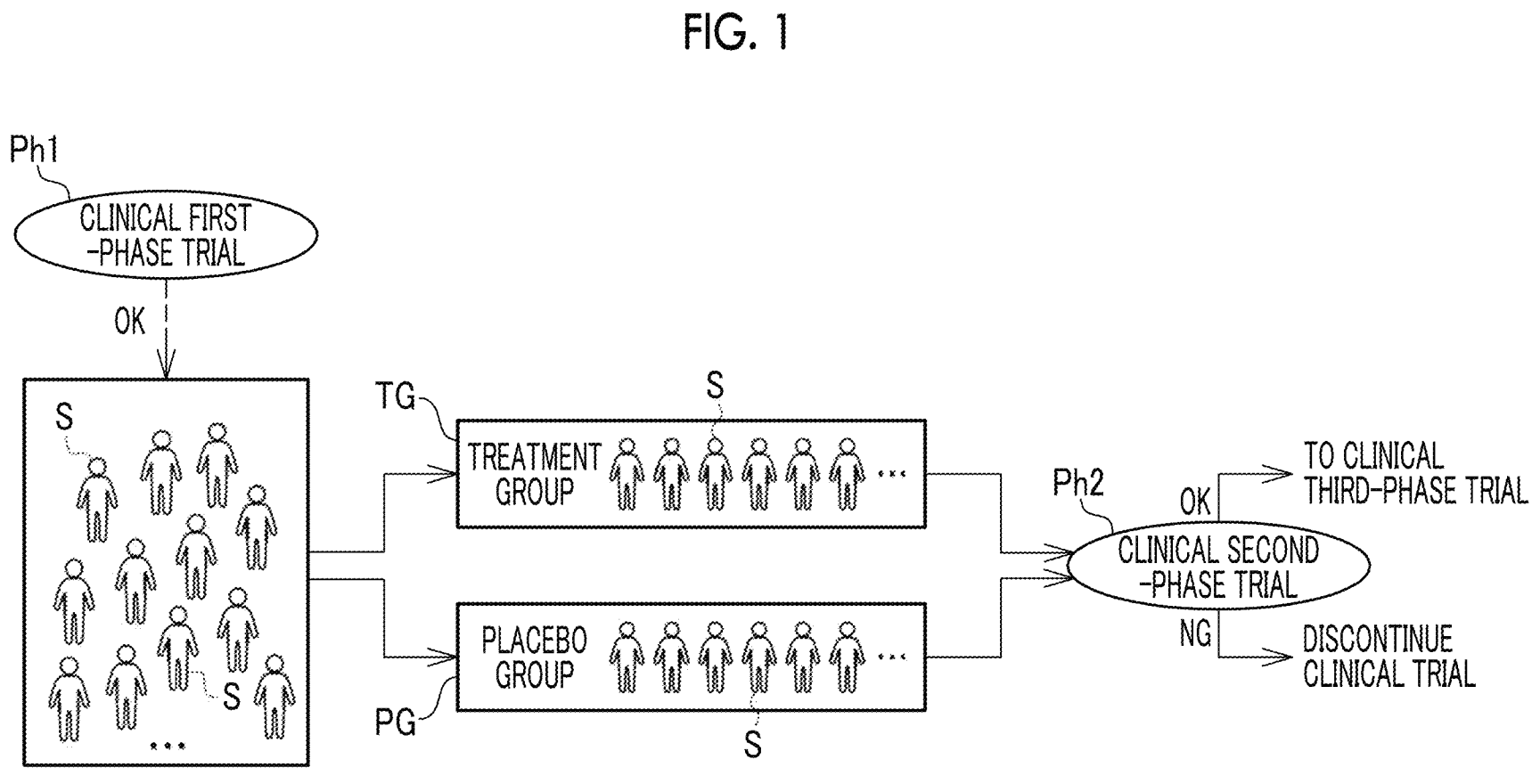
Figure 3:
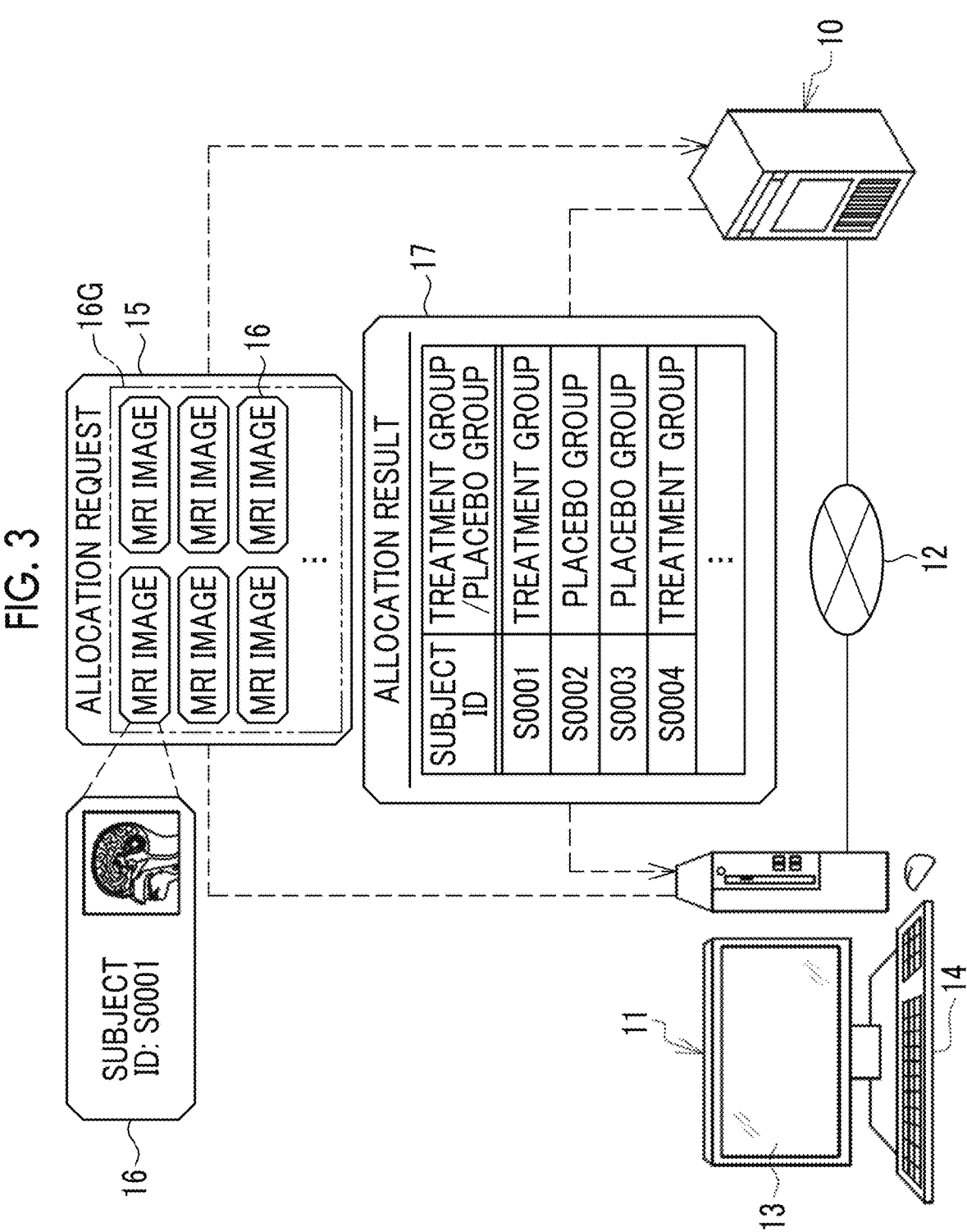
FIG. 3 is a diagram showing a clinical trial support server and an operator terminal, and various data transmitted and received between the clinical trial support server and the operator terminal.

As shown in FIG. 1 as an example, in a clinical trial related to development of an anti-dementia drug for preventing the onset of dementia or for delaying progression of the dementia, first, a clinical first-phase trial Ph1 targeting a small number of healthy adults, mainly to examine safety of a test drug of the anti-dementia drug and its pharmacokinetics is conducted. In a case where the clinical first-phase trial Ph1 is cleared, a relatively small-scale clinical second-phase trial Ph2 is conducted with, for example, subjects S of about several hundred people. Prior to this clinical second-phase trial Ph2, subjects S are allocated to a treatment group TG to which the test drug is administered and a placebo group PG to which a placebo is administered.

Figure 2:
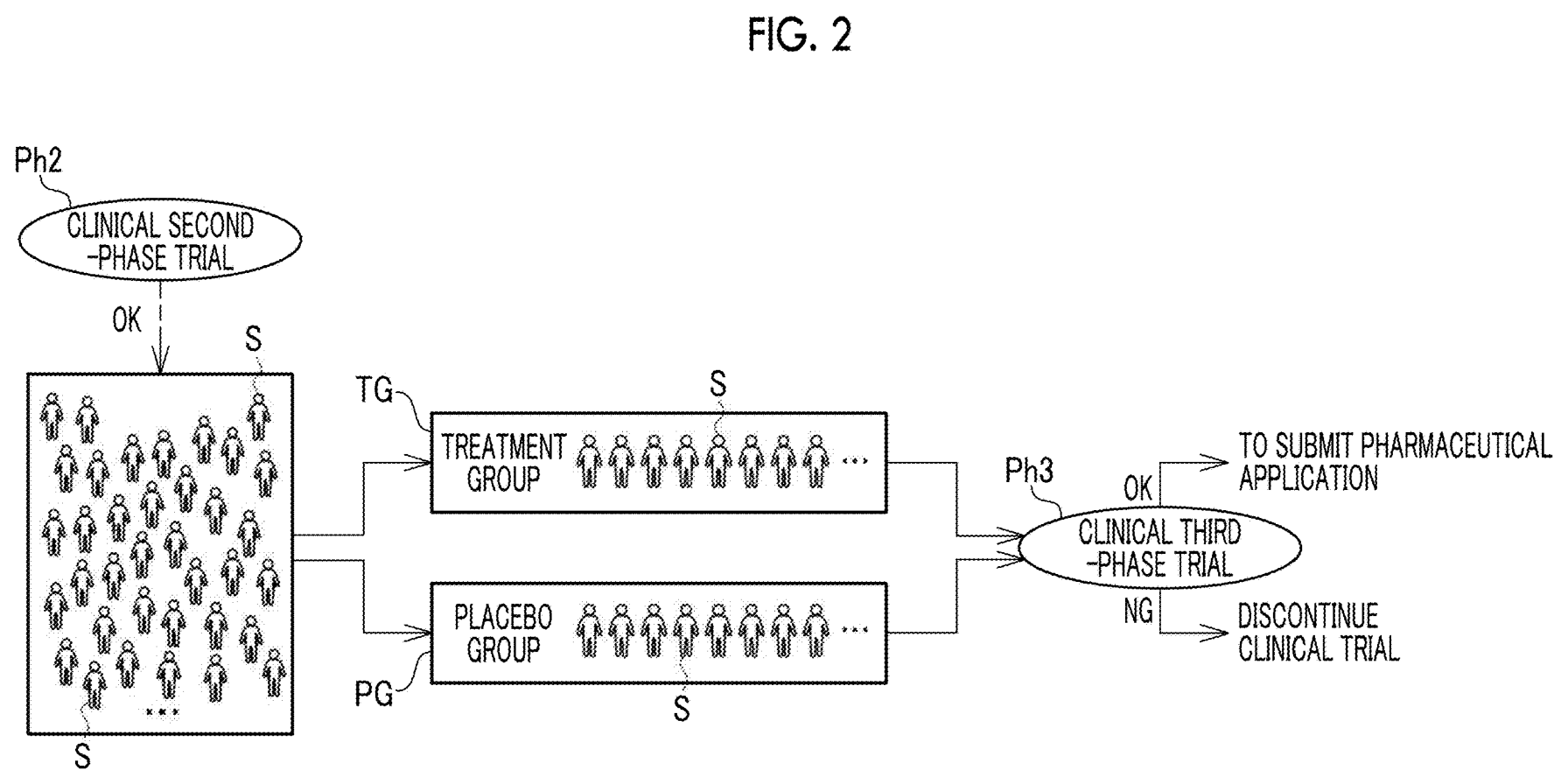

In a case where it is determined that the test drug has no efficacy in the clinical second-phase trial Ph2 (indicated as "NG" in FIG. 1), the clinical trial is discontinued. On the other hand, in a case where it is determined that the test drug has the efficacy in the clinical second-phase trial Ph2 (indicated as "OK" in FIG. 1), as shown in FIG. 2 as an example, a relatively large-scale clinical third-phase trial Ph3 is conducted with, for example, subjects S of about several thousand people. The subjects S are allocated to the treatment group TG and the placebo group PG also in the clinical third-phase trial Ph3, as in the case of the clinical second-phase trial Ph2. Periods of the clinical second-phase trial Ph2 and the clinical third-phase trial Ph3 are both, for example, 18 months.

In a case where it is determined that the test drug has no efficacy in the clinical third-phase trial Ph3 (indicated as "NG" in FIG. 2), the clinical trial is discontinued. On the other hand, in a case where it is determined that the test drug has the efficacy in the clinical third-phase trial Ph3 (indicated as "OK" in FIG. 2), a pharmaceutical application is submitted to the Ministry of Health, Labour and Welfare. Therefore, the clinical trial in the present example is a "therapeutic trial" conducted for the purpose of obtaining approval from the Ministry of Health, Labour and Welfare. Of course, the technology of the present disclosure also includes clinical trials other than the "therapeutic trial".

The dementia is an example of a "target disease" and a "cranial nerve disease" according to the technology of the present disclosure. Examples of the dementia include Alzheimer's dementia, Lewy body dementia, and vascular dementia. The anti-dementia drug may be used for Alzheimer's disease other than Alzheimer's dementia. Specifically, the anti-dementia drug may be a drug that delays progression from a preclinical Alzheimer's disease (PAD) to mild cognitive impairment (MCI) due to Alzheimer's disease, or a drug that delays progression from MCI due to Alzheimer's disease to Alzheimer's disease. As the target disease, a cranial nerve disease such as dementia in the example is preferable.

Diagnostic criteria for the dementia include diagnostic criteria disclosed in "Dementia disease medical care guideline 2017" supervised by the Japanese Society of Neurology, "International Statistical Classification of Diseases and Related Health Problems (ICD)-11", the American Psychiatric Association's "Diagnostic and Statistical Manual of Mental Disorders, Fifth Edition (DSM-5)", and the "National Institute on Aging-Alzheimer's Association workgroup (NIA-AA) criteria". Such diagnostic criteria can be cited, and the contents of which are incorporated in the specification of the present application.

Data related to the diagnostic criteria for the dementia includes cognitive function test data, morphological image test data, brain function image test data, blood/cerebrospinal fluid test data, genetic test data, and the like. The cognitive function test data includes a clinical dementia rating-sum of boxes (hereinafter abbreviated as CDR-SOB) score, a minimental state examination (hereinafter abbreviated as MMSE) score, an Alzheimer's disease assessment scale-cognitive subscale (hereinafter abbreviated as ADAS-Cog) score, and the like. The morphological image test data includes a brain tomographic image obtained by magnetic resonance imaging (MRI) (hereinafter, referred to as an MRI image) 16 (refer to FIG. 3), a tomographic image of the brain obtained by computed tomography (CT) (hereinafter, referred to as a CT image), or the like.

The brain function image test data includes a brain tomographic image obtained by a positron emission tomography (PET) (hereinafter, referred to as a PET image), a brain tomographic image obtained by a single photon emission computed tomography (SPECT) (hereinafter, referred to as a SPECT image), and the like. The blood/cerebrospinal fluid test data includes an amount of phosphorylated tau protein (p-tau) 181 in cerebrospinal fluid (hereinafter, abbreviated as CSF), and the like. The genetic test data includes a test result of a genotype of an ApoE gene, and the like.

As shown in FIG. 3 as an example, a clinical trial support server 10 is a server that supports the allocation of the subjects S to the treatment group TG and the placebo group PG in the clinical second-phase trial Ph2 and the clinical third-phase trial Ph3, and is connected to an operator terminal 11 via a network 12. The clinical trial support server 10 is an example of a "clinical trial support server" according to the technology of the present disclosure. The operator terminal 11 is installed in, for example, a drug development facility and is operated by an operator involved in a clinical trial in the drug development facility. The operator terminal 11 has a display 13 and an input device 14 such as a keyboard and a mouse. The network 12 is, for example, a wide area network (WAN) such as the Internet or a public communication network. In FIG. 3, only one operator terminal 11 is connected to the clinical trial support server 10, but in practice, a plurality of the operator terminals 11 of a plurality of drug development facilities are connected to the clinical trial support server 10.

The operator terminal 11 transmits an allocation request 15 to the clinical trial support server 10. The allocation request 15 is a request for causing the clinical trial support server 10 to allocate the subjects S to the treatment group TG and the placebo group PG in the clinical second-phase trial Ph2 or the clinical third-phase trial Ph3. The allocation request 15 includes an MRI image group 16G, which is a set of MRI images 16 showing brains of the respective subjects S. The MRI image 16 is assigned with a subject identification data (ID) for uniquely identifying the subject S. The MRI image 16 is an example of a "medical image" according to the technology of the present disclosure. In addition, the brain is an example of an "organ" according to the technology of the present disclosure. Although not shown, the allocation request 15 also includes a terminal ID for uniquely identifying the operator terminal 11, which is a transmission source of the allocation request 15.

In a case where the allocation request 15 is received, the clinical trial support server 10 derives an allocation result 17. The allocation result 17 is data in which the treatment group TG or the placebo group PG, which is a result of the allocation, is registered for each subject ID. The clinical trial support server 10 distributes the allocation result 17 to the operator terminal 11, which is the transmission source of the allocation request 15. In a case where the allocation result 17 is received, the operator terminal 11 displays the allocation result 17 on the display 13 such that the operator views the allocation result 17.

Figure 4:
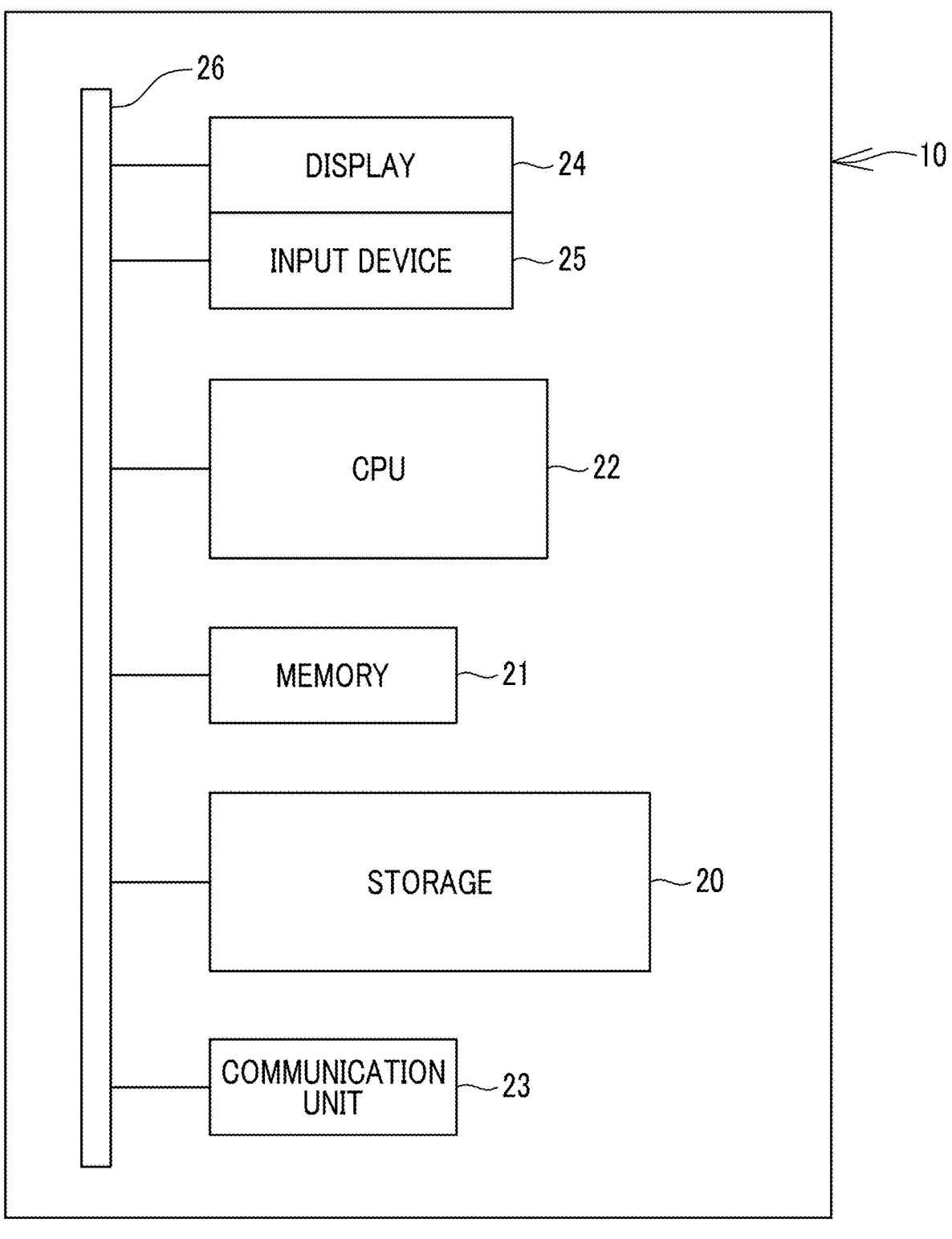
FIG. 4 is a block diagram showing a computer constituting the clinical trial support server.

As shown in FIG. 4 as an example, a computer constituting the clinical trial support server 10 comprises a storage 20, a memory 21, a central processing unit (CPU) 22, a communication unit 23, a display 24, and an input device 25. These units are connected to each other via a bus line 26.

The storage 20 is a hard disk drive that is built in the computer constituting the clinical trial support server 10 or that is connected to the computer through a cable or a network. Alternatively, the storage 20 is a disk array in which a plurality of hard disk drives are continuously mounted. The storage 20 stores a control program such as an operating system, various types of application programs, and various types of data associated with these programs. A solid state drive may be used instead of the hard disk drive.

The memory 21 is a work memory that is used to execute processing by the CPU 22. The CPU 22 loads the program stored in the storage 20 to the memory 21, and executes processing in accordance with the program. Thus, the CPU 22 collectively controls the respective units of the computer. The CPU 22 is an example of a "processor" according to the technology of the present disclosure. The memory 21 may be built in the CPU 22.

The communication unit 23 controls transmission of various types of information to an external device such as the operator terminal 11. The display 24 displays various screens. The various screens have operation functions by a graphical user interface (GUI). The computer constituting the clinical trial support server 10 receives an input of an operation instruction from the input device 25 through the various screens. The input device 25 is, for example, a keyboard, a mouse, a touch panel, and a microphone for voice input.

Figure 5:
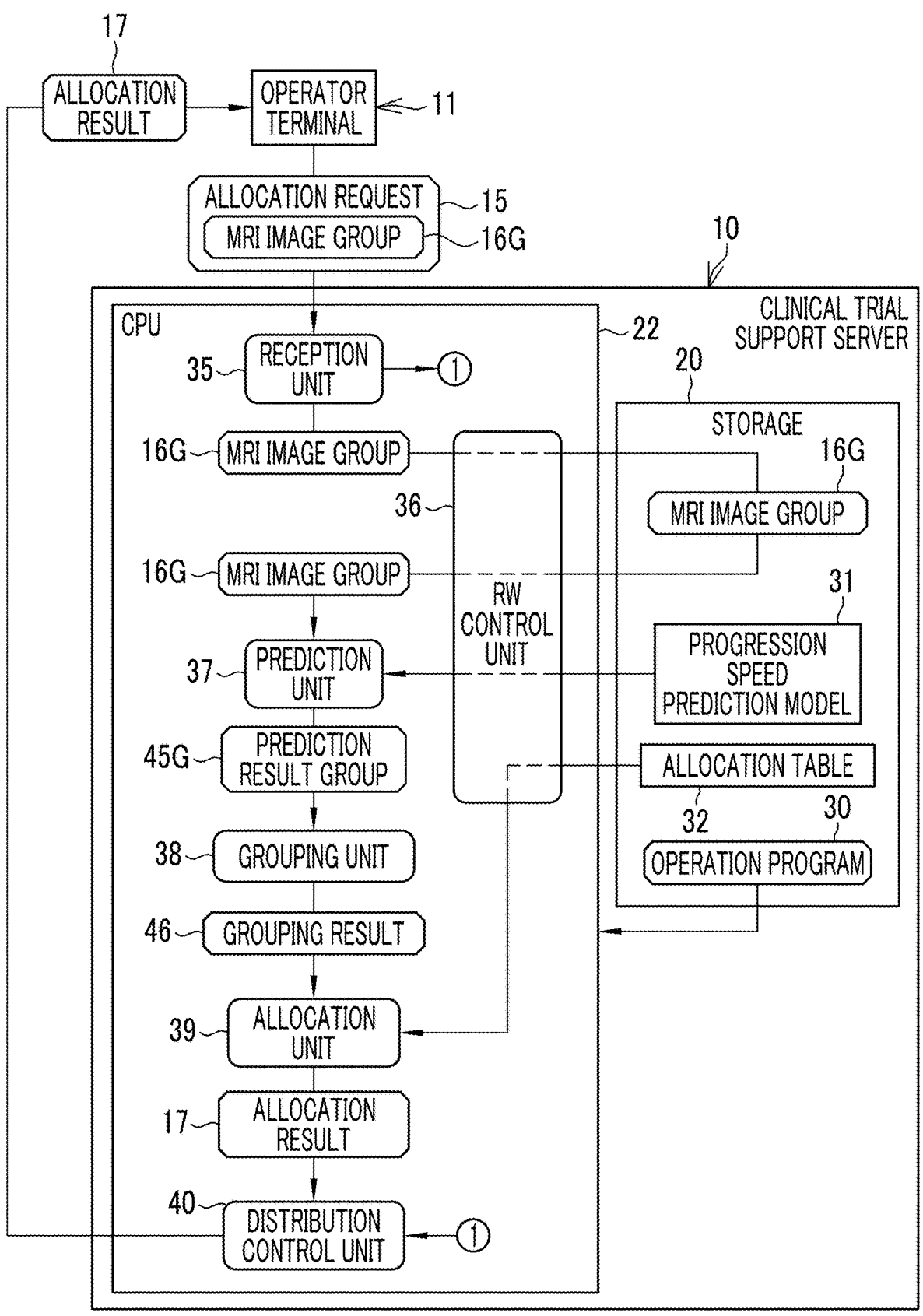
FIG. 5 is a block diagram showing a processing unit of a CPU of the clinical trial support server.

As shown in FIG. 5 as an example, an operation program 30 is stored in the storage 20 of the clinical trial support server 10. The operation program 30 is an application program for causing the computer to function as the clinical trial support server 10. That is, the operation program 30 is an example of an "operation program of a clinical trial support apparatus" according to the technology of the present disclosure. The storage 20 also stores the MRI image group 16G. In addition, the storage 20 also stores a progression speed prediction model 31 and an allocation table 32. The progression speed prediction model 31 is an example of a "trained model" according to the technology of the present disclosure.

In a case where the operation program 30 is activated, the CPU 22 of the computer constituting the clinical trial support server 10 functions as a reception unit 35, a read write (hereinafter, abbreviated as RW) control unit 36, a prediction unit 37, a grouping unit 38, an allocation unit 39, and a distribution control unit 40 in conjunction with the memory 21 and the like.

The reception unit 35 receives the allocation request 15 from the operator terminal 11. As described above, the allocation request 15 includes the MRI image group 16G. Therefore, the reception unit 35 acquires the MRI image group 16G by receiving the allocation request 15. The reception unit 35 outputs the MRI image group 16G to the RW control unit 36. In addition, the reception unit 35 outputs the terminal ID (not shown) of the operator terminal 11 to the distribution control unit 40.

The RW control unit 36 controls the storage of various data in the storage 20 and the reading-out of various data in the storage 20. For example, the RW control unit 36 stores the MRI image group 16G from the reception unit 35 in the storage 20. In addition, the RW control unit 36 reads out the MRI image group 16G from the storage 20, and outputs the MRI image group 16G to the prediction unit 37. In addition, the RW control unit 36 reads out the progression speed prediction model 31 from the storage 20, and outputs the progression speed prediction model 31 to the prediction unit 37. Further, the RW control unit 36 reads out the allocation table 32 from the storage 20, and outputs the allocation table 32 to the allocation unit 39.

The prediction unit 37 uses the progression speed prediction model 31 to predict a progression speed of the dementia of each subject S from all the MRI images 16 constituting the MRI image group 16G. The prediction unit 37 outputs a prediction result group 45G, which is a set of prediction results 45 (see FIG. 6) of the progression speed of the dementia of the respective subjects S, to the grouping unit 38.

The grouping unit 38 divides the subjects S into a plurality of groups according to the prediction result 45. The grouping unit 38 outputs a grouping result 46 to the allocation unit 39.

The allocation unit 39 allocates the subjects S to the treatment group TG and the placebo group PG for each of the plurality of groups based on the allocation table 32. The allocation unit 39 outputs the allocation result 17 to the distribution control unit 40.

The distribution control unit 40 performs control of distributing the allocation result 17 to the operator terminal 11, which is the transmission source of the allocation request 15. In this case, the distribution control unit 40 specifies the operator terminal 11, which is the transmission source of the allocation request 15, based on the terminal ID from the reception unit 35.

Figure 6:
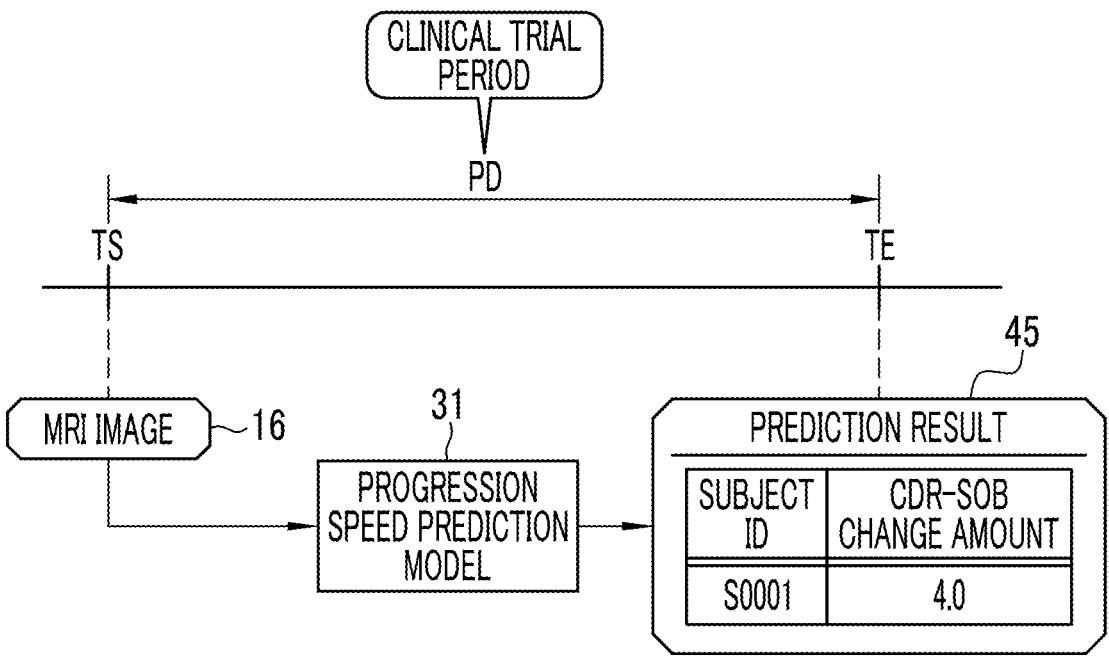
FIG. 6 is a diagram showing processing of a prediction unit and a time point of an MRI image and a prediction result.

As shown in FIG. 6 as an example, the prediction unit 37 inputs the MRI image 16 to the progression speed prediction model 31. Then, the prediction result 45 is output from the progression speed prediction model 31. In the present example, the prediction result 45 is a change amount of the CDR-SOB score (hereinafter, referred to as a CDR-SOB change amount).

The MRI image 16 input to the progression speed prediction model 31 is an image showing the brain of the subject S at a start time point TS of the clinical trial. In addition, the prediction result 45 output from the progression speed prediction model 31 is a prediction result of the CDR-SOB change amount of the subject S at an end time point TE of the clinical trial after a lapse of a clinical trial period PD from the start time point TS. In a case where the CDR-SOB change amount is 0 or more, it is predicted that the dementia of the subject S has progressed at the end time point of the clinical trial. In addition, the larger the CDR-SOB change amount is, the faster the progression of the dementia of the subject S is predicted to be. The prediction result 45 is assigned with the same subject ID as the MRI image 16. The CDR-SOB change amount is an example of a "numerical value indicating a degree of progression of the target disease" and a "change amount of a score of a cognitive function test" according to the technology of the present disclosure. Hereinafter, for convenience of description, the CDR-SOB change amount may be denoted by A. The start time point TS may be strictly a start date of the clinical trial, but a margin such as one week before or after the start date of the clinical trial may be provided.

Figure 7:
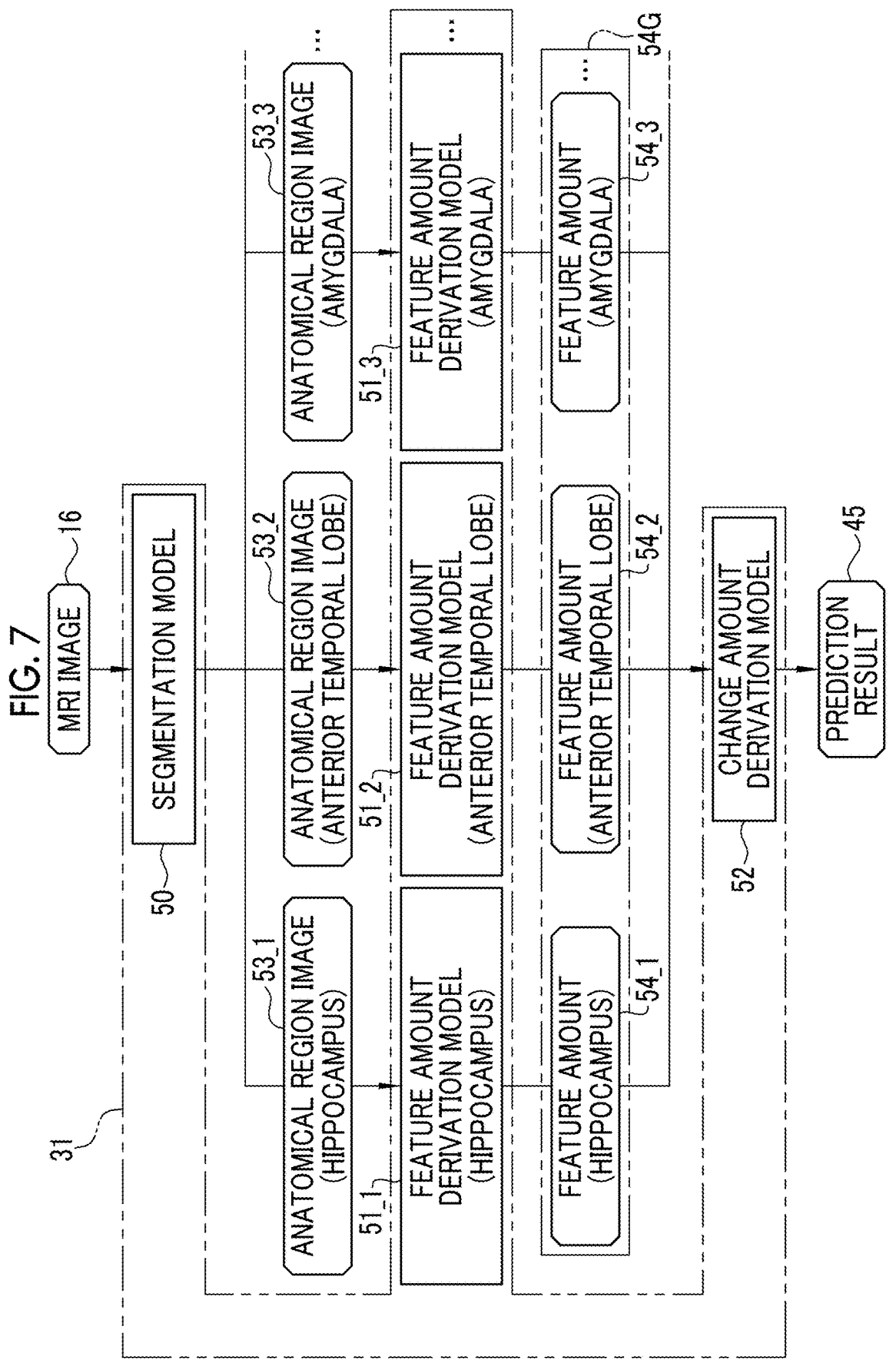
FIG. 7 is a diagram showing details of a progression speed prediction model and processing of the prediction unit.

As shown in FIG. 7 as an example, the progression speed prediction model 31 is composed of a segmentation model 50, a plurality of feature amount derivation models 51, and a change amount derivation model 52. The segmentation model 50 is a trained model that performs so-called semantic segmentation of assigning a label representing each anatomical region of the brain, such as the hippocampus, the anterior temporal lobe, and the amygdala, to each pixel of the brain shown in the MRI image 16. The prediction unit 37 extracts images 53 of a plurality of anatomical regions of the brain (hereinafter, referred to as an anatomical region image) from the MRI image 16 based on the labels assigned by the segmentation model 50. FIG. 7 shows an example in which an anatomical region image 53_1 of the hippocampus, an anatomical region image 53_2 of the anterior temporal lobe, an anatomical region image 53_3 of the amygdala, and the like are extracted. The anterior temporal lobe means a front portion of the temporal lobe. In addition to the hippocampus, the anterior temporal lobe, and the amygdala, for example, anatomical region images of the frontal lobe, the mammillary body, the corpus callosum, the fornix, and the lateral ventricle, and the like may be extracted. It is preferable that the anatomical region images further include images of a plurality of other anatomical regions such as the parahippocampal gyrus, the occipital lobe, the thalamus, and the hypothalamus. For the anatomical regions that are present on the left and right of the brain, such as the hippocampus and the anterior temporal lobe, it is preferable to extract the anatomical region images of the anatomical regions on the left and right, respectively. As disclosed in WO2022/071158A, the anatomical region images preferably include at least an image of the hippocampus, and more preferably include at least an image of the hippocampus and an image of the anterior temporal lobe.

One feature amount derivation model 51 is prepared for each anatomical region of the brain. In FIG. 7, a feature amount derivation model 51_1 of the hippocampus, a feature amount derivation model 51_2 of the anterior temporal lobe, and a feature amount derivation model 51_3 of the amygdala are illustrated. The prediction unit 37 inputs each anatomical region image 53 to a corresponding feature amount derivation model 51. Then, a feature amount 54 of each anatomical region is output from the feature amount derivation model 51. In FIG. 7, a feature amount 54_1 of the hippocampus, a feature amount 54_2 of the anterior temporal lobe, and a feature amount 54_3 of the amygdala are illustrated.

The prediction unit 37 inputs a feature amount group 54G, which is a set of the feature amounts 54 of the respective anatomical regions, to the change amount derivation model 52. Then, the prediction result 45 is output from the change amount derivation model 52. The change amount derivation model 52 is constructed by any method of a neural network, a support vector machine, or boosting.

Figures 8, 9:
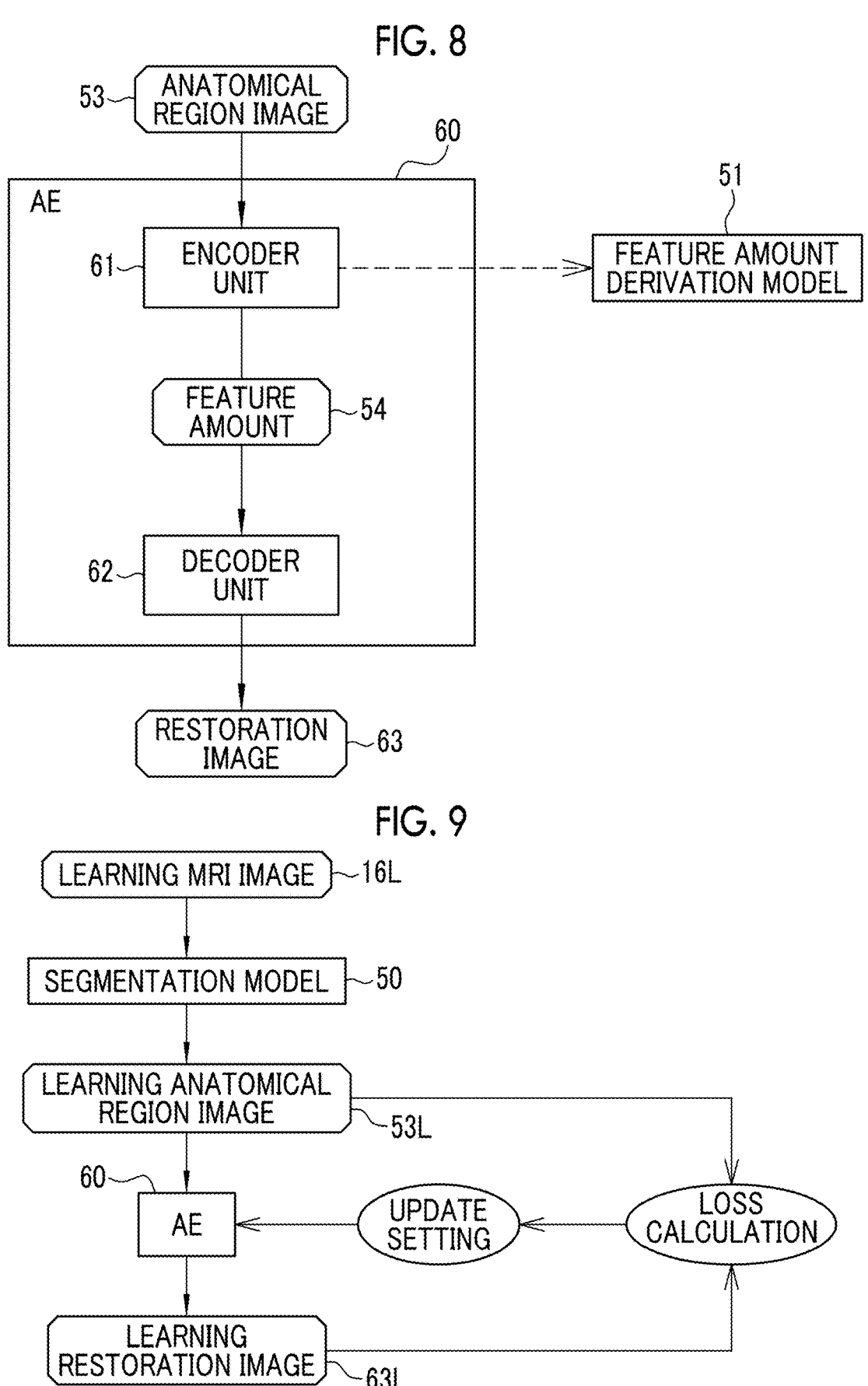
FIG. 8 is a diagram showing a configuration of an auto-encoder and a structure of a feature amount derivation model.
FIG. 9 is a diagram showing an outline of processing in a learning phase of the auto-encoder.

As shown in FIG. 8 as an example, an encoder unit 61 of an auto-encoder (hereinafter, abbreviated as AE) 60 is used in the feature amount derivation model 51. The AE 60 includes the encoder unit 61 and a decoder unit 62. The anatomical region image 53 is input to the encoder unit 61. The encoder unit 61 converts the anatomical region image 53 into the feature amount 54 by performing well-known convolution operation, pooling processing, and the like. The feature amount 54 obtained in this way represents a shape of each anatomical region and a feature of a texture, such as a degree of atrophy of the hippocampus and the presence or absence of a decrease in blood flow metabolism of the anterior temporal lobe. The encoder unit 61 delivers the feature amount 54 to the decoder unit 62. The decoder unit 62 generates a restoration image 63 of the anatomical region image 53 from the feature amount 54.

As shown in FIG. 9 as an example, the AE 60 is trained by receiving a learning anatomical region image 53L in a learning phase before the encoder unit 61 is diverted to the feature amount derivation model 51. The learning anatomical region image 53L is an image extracted from a learning MRI image 16L by using the segmentation model 50. The learning MRI image 16L is an MRI image 16 of a dementia patient who satisfies participation conditions of the clinical trial among dementia patients whose MRI images 16 and the like are registered in a database such as Alzheimer's Disease Neuroimaging Initiative (ADNI). Examples of the participation conditions of the clinical trial include positive amyloid p in the CSF test and an MMSE score of 26 points or less. The learning MRI image 16L is an example of "learning input data" according to the technology of the present disclosure. In addition, the dementia patient is an example of a "target disease patient" according to the technology of the present disclosure.

The AE 60 outputs a learning restoration image 63L in response to the learning anatomical region image 53L. Loss calculation of the AE 60 using a loss function is performed based on the learning anatomical region image 53L and the learning restoration image 63L. Then, update setting of various coefficients (coefficients of the filter of the convolution operation and the like) of the AE 60 is performed according to a result of the loss calculation, and the AE 60 is updated according to the update setting.

In the learning phase of the AE 60, while exchanging the learning anatomical region image 53L, a series of processing including inputting of the learning anatomical region image 53L to the AE 60, outputting of the learning restoration image 63L from the AE 60, the loss calculation, the update setting, and updating of the AE 60 is repeatedly performed. The repetition of the series of processing is ended in a case where accuracy of restoration from the learning anatomical region image 53L to the learning restoration image 63L reaches a predetermined set level. The encoder unit 61 of the AE 60 in which the accuracy of restoration has reached the set level in this way is used in the prediction unit 37 as a part of the progression speed prediction model 31. The learning may be ended in a case where the above-described series of processing is repeated a set number of times, regardless of the restoration accuracy from the learning anatomical region image 53L to the learning restoration image 63L.

Figures 10, 11:
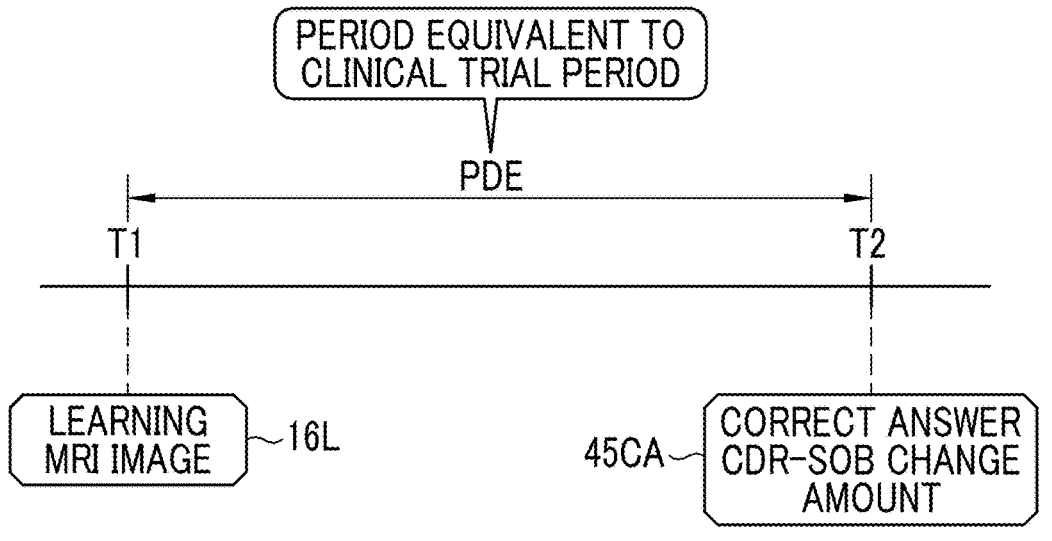
FIG. 10 is a diagram showing an outline of processing in a learning phase of a change amount derivation model.
FIG. 11 is a diagram showing a time point of a learning MRI image and a correct answer CDR-SOB change amount.

As shown in FIG. 10 as an example, the change amount derivation model 52 is trained by using learning data 70. The learning data 70 is a set of a learning feature amount group 54GL and a correct answer CDR-SOB change amount 45CA. The learning feature amount group 54GL is obtained by inputting the learning anatomical region image 53L of each anatomical region extracted from the learning MRI image 16L to each trained feature amount derivation model 51. The correct answer CDR-SOB change amount 45CA is an actual CDR-SOB change amount of the dementia patient of the learning MRI image 16L from which the learning feature amount group 54GL is obtained. The correct answer CDR-SOB change amount 45CA is an example of "correct answer data" according to the technology of the present disclosure.

In the learning phase, the learning feature amount group 54GL is input to the change amount derivation model 52. The change amount derivation model 52 outputs the learning prediction result 45L in response to the learning feature amount group 54GL. Loss calculation of the change amount derivation model 52 using a loss function is performed based on the learning prediction result 45L and the correct answer CDR-SOB change amount 45CA. Then, update setting of various coefficients of the change amount derivation model 52 is performed according to a result of the loss calculation, and the change amount derivation model 52 is updated according to the update setting.

In the learning phase of the change amount derivation model 52, while exchanging the learning data 70, a series of processing including inputting of the learning feature amount group 54GL to the change amount derivation model 52, outputting of the learning prediction result 45L from the change amount derivation model 52, the loss calculation, the update setting, and updating of the change amount derivation model 52 is repeatedly performed. The repetition of the series of processing is ended in a case where prediction accuracy of the learning prediction result 45L for the correct answer CDR-SOB change amount 45CA reaches a predetermined set level. The change amount derivation model 52 in which the prediction accuracy has reached the set level in this way is used in the prediction unit 37 as a part of the progression speed prediction model 31. The learning may be ended in a case where the above-described series of processing is repeated a set number of times, regardless of the prediction accuracy of the learning prediction result 45L for the correct answer CDR-SOB change amount 45CA.

As shown in FIG. 11 as an example, the learning MRI image 16L is an image showing the brain of the dementia patient at a first time point T1. In addition, the correct answer CDR-SOB change amount 45CA is an actual CDR-SOB change amount of the dementia patient at a second time point T2 after a lapse of a period PDE equivalent to the clinical trial period PD from the first time point T1. For example, in a case where the CDR-SOB score of the dementia patient at the first time point T1 is 22 and the CDR-SOB score at the second time point T2 is 25, the correct answer CDR-SOB change amount 45CA is 25–22=3. The period PDE equivalent to the clinical trial period PD is a period including the clinical trial period PD and having an appropriate margin added to the clinical trial period PD. For example, in a case where the clinical trial period PD is 18 months, the period PDE equivalent to the clinical trial period PD is 12 months to 24 months, which is ±6 months in 18 months.

As shown in FIG. 12 as an example, the grouping unit 38 divides the subjects S into any of groups 1 to 18 according to the CDR-SOB change amount of the prediction result 45. The grouping unit 38 allocates, for example, the subjects S whose CDR-SOB change amount is smaller than –3.0 (Δ<–3.0) in the group 1, and allocates, for example, the subjects S whose CDR-SOB change amount is –2.0 or more and smaller than –1.5 (–2.0≤Δ<–1.5) in the group 4. In addition, the grouping unit 38 allocates, for example, the subjects S whose CDR-SOB change amount is 3.5 or more and smaller than 4.0 (3.5≤Δ<4.0) in the group 15, and allocates, for example, the subjects S whose CDR-SOB change amount is more than 5.0 (5.0<Δ) in the group 18. As described above, the groups 1 to 18 are mainly defined by a range set in increments of 0.5 in the CDR-SOB change amount of –3.0 to 5.0.

The grouping result 46 is data in which the subject ID of the subject S is registered for each group. For example, since the CDR-SOB change amount of the subject S whose subject ID is S0001 is 4.0, the grouping unit 38 registers S0001 in the group 16. In addition, for example, since the CDR-SOB change amount of the subject S whose subject ID is S0004 is –1.7, the grouping unit 38 registers S0004 in the group 4.

As shown in FIG. 13 as an example, the allocation table 32 is a table in which an allocation rule for each group is registered. The allocation rule is based on a block randomization method in units of two persons. For example, the allocation rule of the group 1 is a content in which, for first, second, and fourth pairs of two subjects S, a first subject S is allocated to the treatment group TG and a second subject S is allocated to the placebo group PG. In addition, the content is that, for third, fifth, and sixth pairs of two subjects S, a first subject S is allocated to the placebo group PG and a second subject S is allocated to the treatment group TG. For example, the allocation rule of the group 16 is a content in which, for first to fourth and sixth pairs of two subjects S, a first subject S is allocated to the treatment group TG and a second subject S is allocated to the placebo group PG. In addition, the content is that, for a fifth pair of two subjects S, a first subject S is allocated to the placebo group PG and a second subject S is allocated to the treatment group TG.

Figure 14:
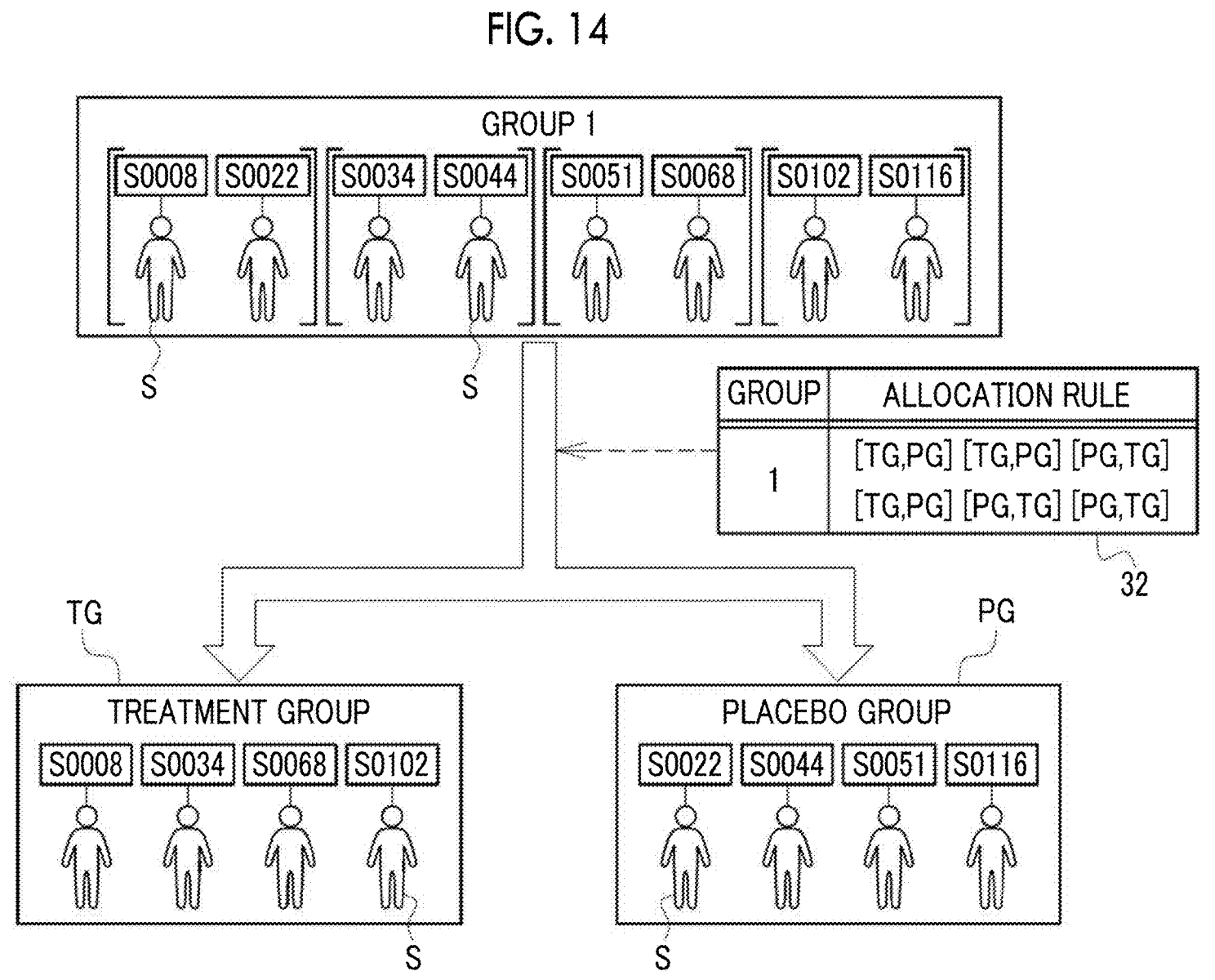

FIG. 14 shows an example of a state in which the subjects S of the group 1 are allocated to the treatment group TG and the placebo group PG according to the allocation rule of the allocation table 32. FIG. 14 illustrates a case where eight subjects S whose subject IDs are S0008, S0022, S0034, S0044, S0051, S0068, S0102, and S0116 are allocated. In this case, the allocation unit 39 allocates the subject S of S0008, out of the two subjects S of the first pair, that is, S0008 and S0022, to the treatment group TG and allocates the subject S of S0022 to the placebo group PG according to the allocation rule of allocating the first subject S to the treatment group TG and allocating the second subject S to the placebo group PG. Similarly, the subject S of S0034, out of the two subjects S of the second pair, that is, S0034 and S0044, is allocated to the treatment group TG, and the subject S of S0044 is allocated to the placebo group PG. Further, the subject S of S0102, out of the two subjects S of the fourth pair, that is, S0102 and S0116, is allocated to the treatment group TG, and the subject S of S0116 is allocated to the placebo group PG. In addition, the allocation unit 39 allocates the subject S of S0051, out of the two subjects S of the third pair, that is, S0051 and S0068, to the placebo group PG and allocates the subject S of S0068 to the treatment group TG according to the allocation rule of allocating the first subject S to the placebo group PG and allocating the second subject S to the treatment group TG.

Figure 15:
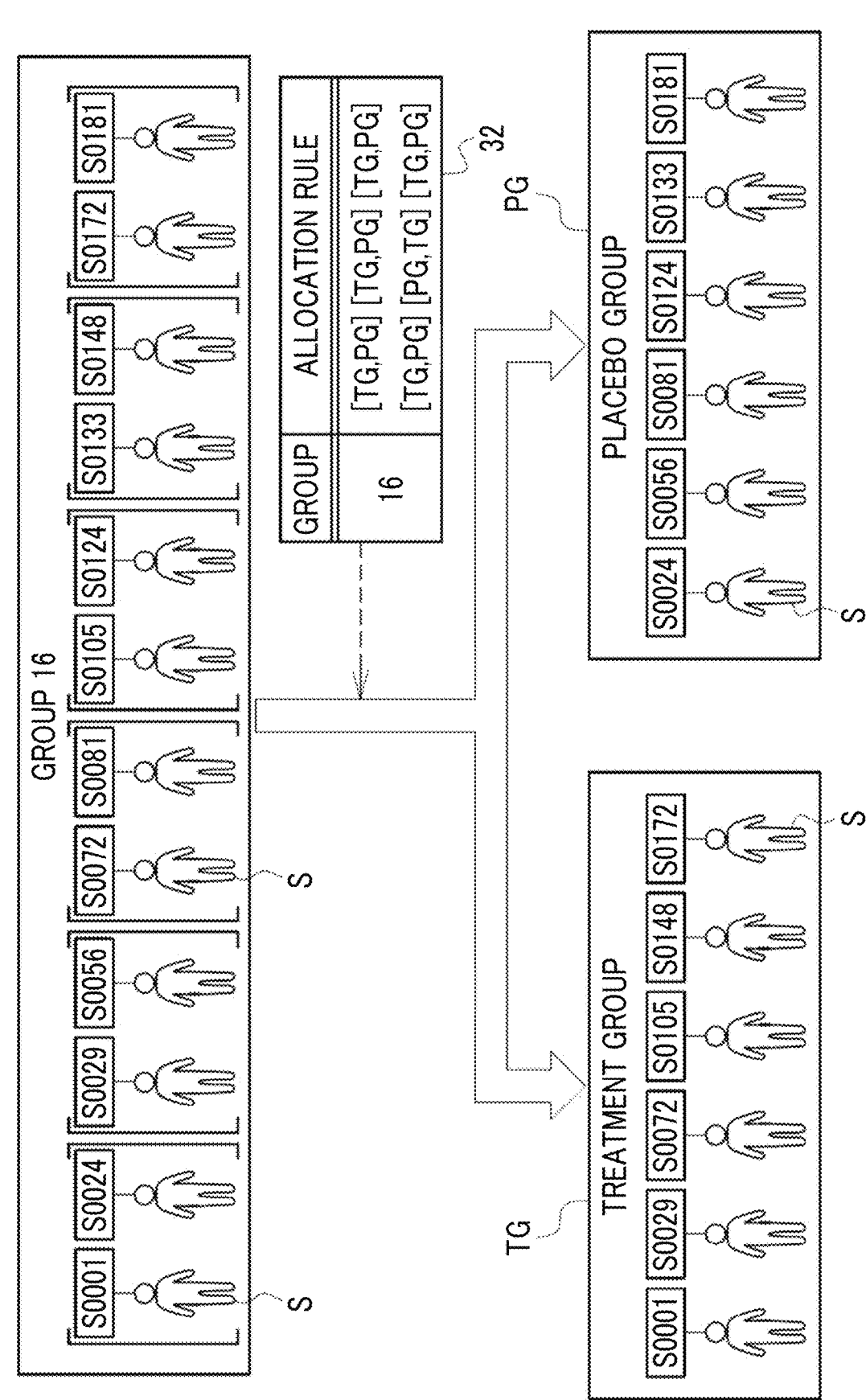
FIG. 15 is a diagram showing processing of the allocation unit.

FIG. 15 shows an example of a state in which the subjects S of the group 16 are allocated to the treatment group TG and the placebo group PG according to the allocation rule of the allocation table 32. FIG. 15 illustrates a case where 12 subjects S whose subject IDs are S0001, S0024, S0029, S0056, S0072, S0081, S0105, S0124, S0133, S0148, S0172, and S0181 are allocated. In this case, the allocation unit 39 allocates the subject S of S0001, out of the two subjects S of the first pair, that is, S0001 and S0024, to the treatment group TG and allocates the subject S of S0024 to the placebo group PG according to the allocation rule of allocating the first subject S to the treatment group TG and allocating the second subject S to the placebo group PG. Similarly, the subject S of S0029, out of the two subjects S of the second pair, that is, S0029 and S0056, is allocated to the treatment group TG, and the subject S of S0056 is allocated to the placebo group PG. The subject S of S0072, out of the two subjects S of the third pair, that is, S0072 and S0081, is allocated to the treatment group TG, and the subject S of S0081 is allocated to the placebo group PG. The subject S of S0105, out of the two subjects S of the fourth pair, that is, S0105 and S0124, is allocated to the treatment group TG, and the subject S of S0124 is allocated to the placebo group PG. Further, the subject S of S0172, out of the two subjects S of the sixth pair, that is, S0172 and S0181, is allocated to the treatment group TG, and the subject S of S0181 is allocated to the placebo group PG. In addition, the allocation unit 39 allocates the subject S of S0133, out of the two subjects S of the fifth pair, that is, S0133 and S0148, to the placebo group PG and allocates the subject S of S0148 to the treatment group TG according to the allocation rule of allocating the first subject S to the placebo group PG and allocating the second subject S to the treatment group TG. In this way, the allocation unit 39 allocates the subjects S of each of the groups 1 to 18 to the treatment group TG and the placebo group PG by using the block randomization method. Such an allocation method is called a stratified randomization method.

Figure 16:
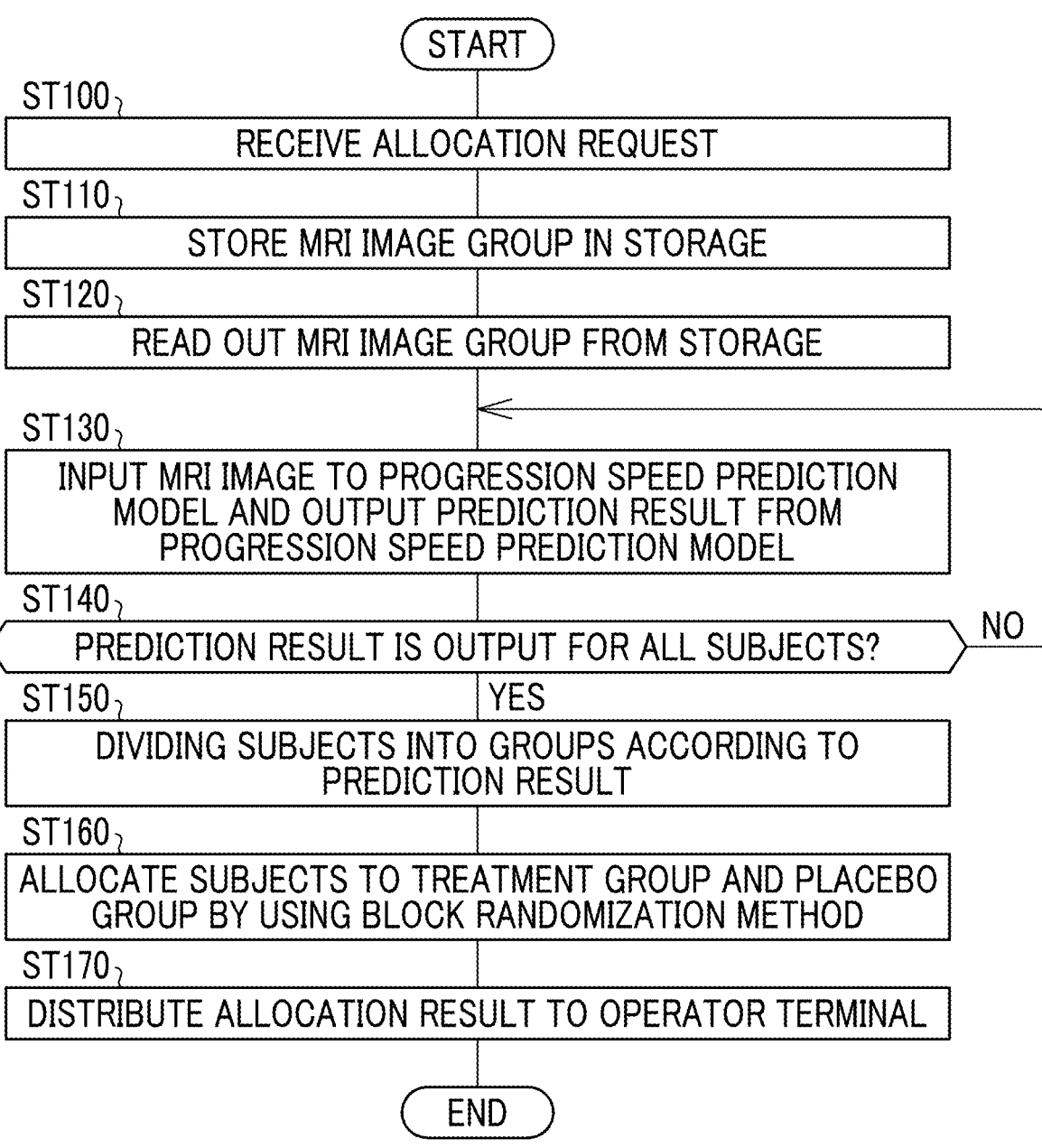
FIG. 16 is a flowchart showing a processing procedure of the clinical trial support server.

Next, an operation according to the configuration will be described with reference to a flowchart in FIG. 16. First, in a case where the operation program 30 is activated in the clinical trial support server 10, as shown in FIG. 5, the CPU 22 of the clinical trial support server 10 functions as the reception unit 35, the RW control unit 36, the prediction unit 37, the grouping unit 38, the allocation unit 39, and the distribution control unit 40.

The operator operates the input device 14 of the operator terminal 11 to transmit the allocation request 15 including the MRI image group 16G, which is a set of the MRI images 16 of the subjects S of the test drug for the dementia, to the clinical trial support server 10.

In the clinical trial support server 10, the allocation request 15 from the operator terminal 11 is received by the reception unit 35 (step ST100). The MRI image group 16G included in the allocation request 15 is output from the reception unit 35 to the RW control unit 36 and is stored in the storage 20 under the control of the RW control unit 36 (step ST110).

The MRI image group 16G is read out from the storage 20 by the RW control unit 36 (step ST120). The MRI image group 16G is output from the RW control unit 36 to the prediction unit 37.

As shown in FIG. 6, in the prediction unit 37, the MRI image 16 is input to the progression speed prediction model 31, and thus the prediction result 45 is output from the progression speed prediction model 31 (step ST130). The process of step ST130 is repeated as long as the prediction result 45 is not output for all the subjects S (NO in step ST140).

In a case where the prediction result 45 is output for all the subjects S (YES in step ST140), the prediction result group 45G, which is a set of the plurality of prediction results 45, is output from the prediction unit 37 to the grouping unit 38. As shown in FIG. 12, in the grouping unit 38, the subjects S are divided into any of the groups 1 to 18 according to the prediction result 45 (step ST150). The grouping result 46 is output from the grouping unit 38 to the allocation unit 39.

Subsequently, as shown in FIGS. 14 and 15, in the allocation unit 39, the subjects S are allocated to the treatment group TG and the placebo group PG for each of the groups 1 to 18 by using the block randomization method (step ST160). The allocation result 17 is output from the allocation unit 39 to the distribution control unit 40. The allocation result 17 is distributed to the operator terminal 11, which is the transmission source of the allocation request 15, under the control of the distribution control unit 40 (step ST170).

The display 13 of the operator terminal 11 displays the allocation result 17. The operator views the allocation result 17, allocates the subjects S to the treatment group TG and the placebo group PG according to the allocation result 17, and performs the clinical second-phase trial Ph2 or the clinical third-phase trial Ph3.

As described above, the CPU 22 of the clinical trial support server 10 comprises the prediction unit 37, the grouping unit 38, and the allocation unit 39. The prediction unit 37 uses the progression speed prediction model 31 to predict the CDR-SOB change amount for the subject S of the test drug for dementia. The grouping unit 38 divides the subjects S into any of the groups 1 to 18 according to the prediction result 45 of the CDR-SOB change amount. The allocation unit 39 allocates the subjects S to the treatment group TG and the placebo group PG for each of the groups 1 to 18.

Therefore, the risk that the bias between the subjects S whose progression of the dementia is relatively fast and the subjects S whose progression of the dementia is relatively slow occurs between the treatment group TG and the placebo group PG is reduced. As a result, the risk that many subjects S whose progression of the dementia is relatively slow are allocated to the treatment group TG, and many subjects S whose progression of the dementia is relatively fast are allocated to the placebo group PG, resulting in an overestimation of the efficacy of the test drug is reduced. In addition, the risk that many subjects S whose progression of the dementia is relatively fast are allocated to the treatment group TG, and many subjects S whose progression of the dementia is relatively slow are allocated to the placebo group PG, resulting in an underestimation of the efficacy of the test drug is also reduced. Therefore, it is possible to contribute to the legitimate evaluation of the efficacy of the test drug for the dementia.

The risk that the bias between the subjects S whose progression of the dementia is relatively fast and the subjects S whose progression of the dementia is relatively slow occurs between the treatment group TG and the placebo group PG is higher in the clinical second-phase trial Ph2 with a relatively small number of the subjects S. Therefore, in a case where the technology of the present disclosure is applied to the clinical second-phase trial Ph2, a more remarkable effect can be obtained.

The allocation unit 39 allocates the subjects S to the treatment group TG and the placebo group PG by using the block randomization method. Therefore, the risk that the bias between the subjects whose progression of the dementia is relatively fast and the subjects whose progression of the dementia is relatively slow occurs between the treatment group TG and the placebo group PG is further reduced, and as a result, it is possible to further contribute to the legitimate evaluation of the efficacy of the test drug for the dementia.

As shown in FIGS. 9 to 11, the progression speed prediction model 31 is a model that has been trained by using the learning MRI image 16L of the dementia patient at the first time point T1 as the learning input data and the correct answer CDR-SOB change amount 45CA, which is the CDR-SOB change amount of the dementia patient at the second time point T2 after the lapse of the period PDE equivalent to the clinical trial period PD from the first time point T1, as the correct answer data. As shown in FIG. 6, the prediction unit 37 inputs the MRI image 16 of the subject S at the start time point TS of the clinical trial to the progression speed prediction model 31, and outputs the CDR-SOB change amount of the subject S at the end time point TE of the clinical trial from the progression speed prediction model 31 as the prediction result 45.

The MRI image 16, which is a medical image showing the brain, is captured for almost all the dementia patients. In addition, the CDR-SOB is taken for almost all the dementia patients. Therefore, in a case where the learning MRI image 16L of the dementia patient is used as the learning input data and the correct answer CDR-SOB change amount 45CA is used as the correct answer data, there is no shortage of the learning data 70 of the progression speed prediction model 31, and the learning of the progression speed prediction model 31 proceeds. Further, the MRI image 16 can be captured in several minutes as long as the apparatus is available. Therefore, the prediction result 45 can be relatively easily output from the progression speed prediction model 31.

The change amount of the score of the cognitive function test, particularly the CDR-SOB change amount, has long been commonly used to determine the success or failure of the clinical trial. Therefore, in a case where the CDR-SOB change amount is used as the numerical value indicating the degree of progression of dementia of the subject S at the end time point TE of the clinical trial as in the present example, it is possible to determine the success or failure of the clinical trial based on the same criteria as in the related art.

The progression speed prediction model 31 extracts the plurality of anatomical region images 53, which are images of a plurality of anatomical regions of the brain, from the MRI image 16 at the start time point TS of the clinical trial by the segmentation model 50. Then, the anatomical region image 53 is input to the feature amount derivation model 51 prepared for each anatomical region, and the feature amount 54 of the anatomical region is output from the feature amount derivation model 51. Therefore, the progression speed of the dementia can be predicted based on the feature amounts obtained from the plurality of anatomical regions of the brain, and the prediction accuracy of the prediction result 45 can be increased.

In order to verify the effect of the technology of the present disclosure, about 500 dementia patients who satisfy the general participation conditions of the clinical trial among the dementia patients registered in ADNI were selected as the subjects S. Then, the clinical second-phase trial Ph2 and the clinical third-phase trial Ph3 were simulated 10,000 times for the selected subjects S.

Figure 17:
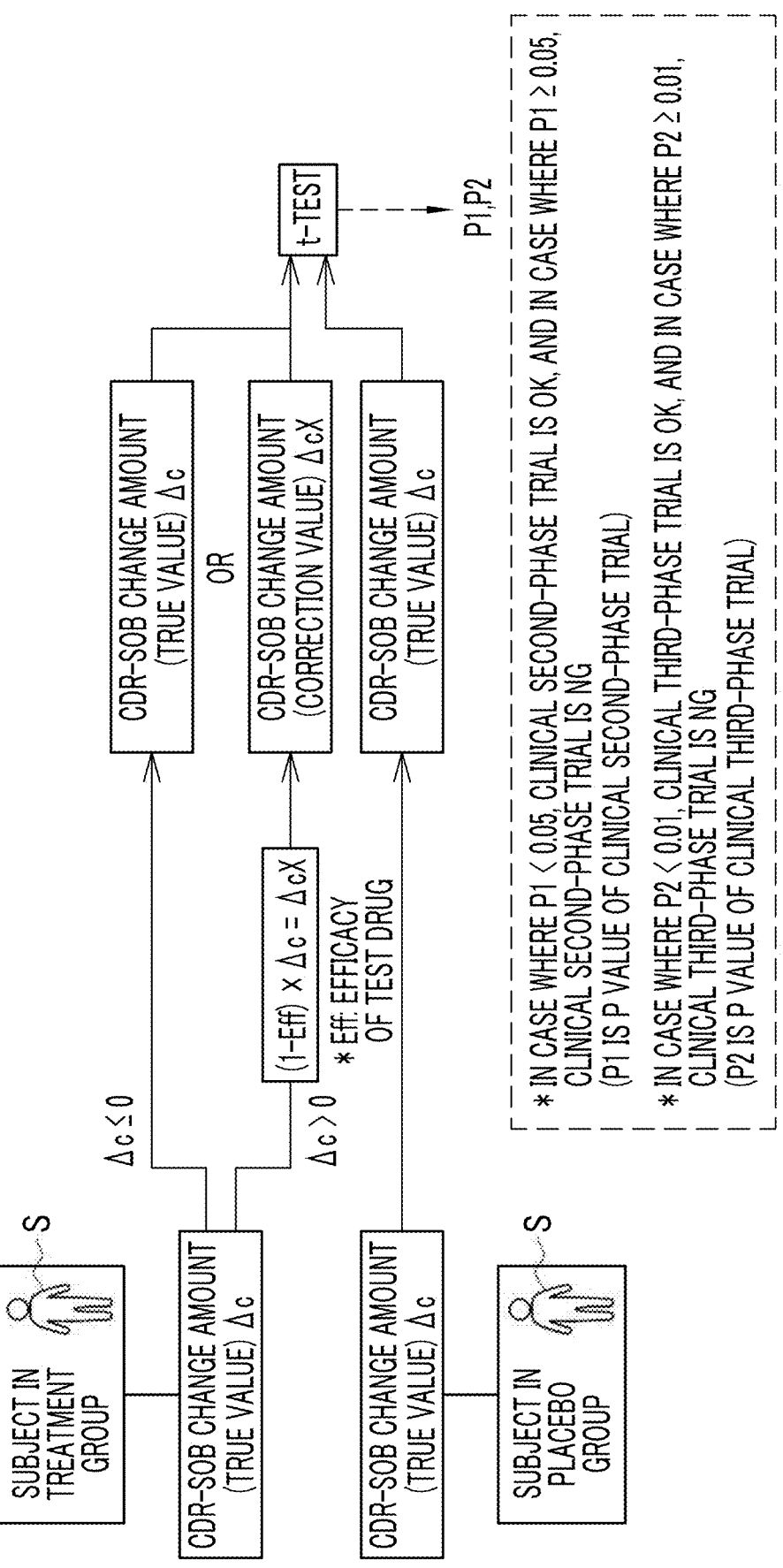
FIG. 17 is a diagram showing details of a simulation for verifying an effect of the technology of the present disclosure.

As shown in FIG. 17 as an example, first, among the subjects S allocated to the treatment group TG, for the subject S whose actual CDR-SOB change amount (true value) $\Delta c$ registered in ADNI is 0 or less, that is, the subject S whose dementia has not progressed, the CDR-SOB change amount (true value) $\Delta c$ is maintained without being corrected. Similarly, the CDR-SOB change amount (true value) $\Delta c$ is maintained without being corrected for the subject S allocated to the placebo group PG. On the other hand, among the subjects S allocated to the treatment group TG, for the subject S whose actual CDR-SOB change amount (true value) $\Delta c$ is larger than 0, that is, the subject S whose dementia has progressed, the CDR-SOB change amount (true value) $\Delta c$ is corrected by the efficacy Eff of the test drug to obtain a CDR-SOB change amount (correction value) $\Delta cX$. Specifically, the CDR-SOB change amount (correction value) $\Delta cX$ is obtained by multiplying the CDR-SOB change amount (true value) $\Delta c$ by (1-Eff).

A t-test was performed using the actual CDR-SOB change amount (true value) $\Delta c$ or the CDR-SOB change amount (correction value) $\Delta cX$ of the subject S allocated to the treatment group TG, and the actual CDR-SOB change amount (true value) $\Delta c$ of the subject S allocated to the placebo group PG. Then, P1, which is a P value of the clinical second-phase trial Ph2, and P2, which is a P value of the clinical third-phase trial Ph3, were calculated. In a case where P1 was smaller than 0.05 (P1<0.05), it was determined that the test drug had an efficacy (cleared the clinical second-phase trial Ph2, indicated as "OK" in FIG. 17, and the same applies to FIGS. 18 to 20), and in a case where P1 was 0.05 or more (P1≥0.05), it was determined that the test drug had no efficacy (did not clear the clinical second-phase trial Ph2, indicated as "NG" in FIG. 17, and the same applies to FIGS. 18 to 20). In addition, in a case where P2 was smaller than 0.01 (P2<0.01), it was determined that the test drug had an efficacy (cleared the clinical third-phase trial Ph3, indicated as "OK" in FIG. 17, and the same applies to FIGS. 18 to 20), and in a case where P2 was 0.01 or more (P2≥0.01), it was determined that the test drug had no efficacy (did not clear the clinical third-phase trial Ph3, indicated as "NG" in FIG. 17, and the same applies to FIGS. 18 to 20).

FIG. 18 shows a probability that P2≥0.01 (did not clear the clinical third-phase trial Ph3) in a state in which P1<0.05 (cleared the clinical second-phase trial Ph2) in a case where the efficacy Eff of the test drug was changed from 0 to 0.4 in increments of 0.05 for each of a method of a comparative example, a method according to the technology of the present disclosure in which the subjects S are randomized by stratification based on the prediction result 45, and a method of stratified randomization based on the actual CDR-SOB change amount (true value) $\Delta c$. The method of the comparative example is a method of randomly allocating all the subjects S who are not divided into groups into the treatment group TG and the placebo group PG without grouping the subjects S according to the prediction result 45 and allocating the subjects S to the treatment group TG and the placebo group PG for each group, unlike the method according to the technology of the present disclosure. The probability that P2≥0.01 in a state in which P1<0.05 is, in other words, a probability that the efficacy of the test drug is overestimated in the clinical second-phase trial Ph2.

According to FIG. 18, it can be seen that the probability that P2≥0.01 in a state in which P1<0.05 in the method according to the technology of the present disclosure is generally lower than the probability that P2≥0.01 in a state in which P1<0.05 in the method of the comparative example. Therefore, according to the technology of the present disclosure, it has been confirmed that the risk that the efficacy of the test drug is overestimated is reduced.

Figure 19:
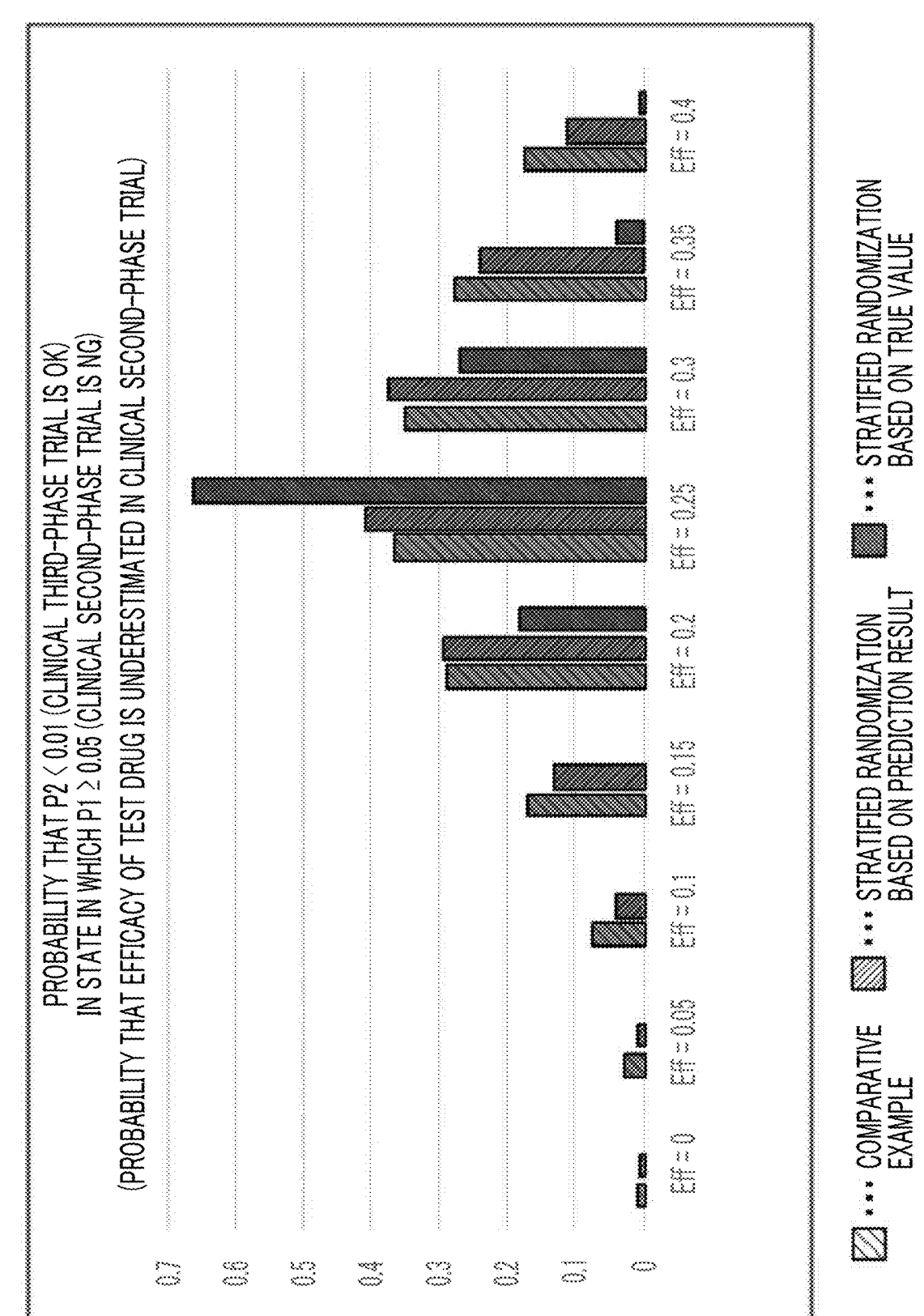
FIG. 19 is a graph showing a probability that an efficacy of a test drug is underestimated in the clinical second-phase trial.

FIG. 19 shows a probability that P2<0.01 (cleared the clinical third-phase trial Ph3) in a state in which P1≥0.05 (did not clear the clinical second-phase trial Ph2) in a case where the efficacy Eff of the test drug was changed from 0 to 0.4 in increments of 0.05 for each of the method of the comparative example, the method according to the technology of the present disclosure in which the subjects S are randomized by stratification based on the prediction result 45, and the method of stratified randomization based on the actual CDR-SOB change amount (true value) $\Delta c$. The probability that P2<0.01 in a state in which P1≥0.05 is, in other words, a probability that the efficacy of the test drug is underestimated in the clinical second-phase trial Ph2.

According to FIG. 19, it can be seen that the probability that P2<0.01 in a state in which P1≥0.05 in the method according to the technology of the present disclosure is mostly lower than the probability that P2<0.01 in a state in which P1≥0.05 in the method of the comparative example. Therefore, according to the technology of the present disclosure, it has been confirmed that the risk that the efficacy of the test drug is underestimated is reduced.

Figure 20:
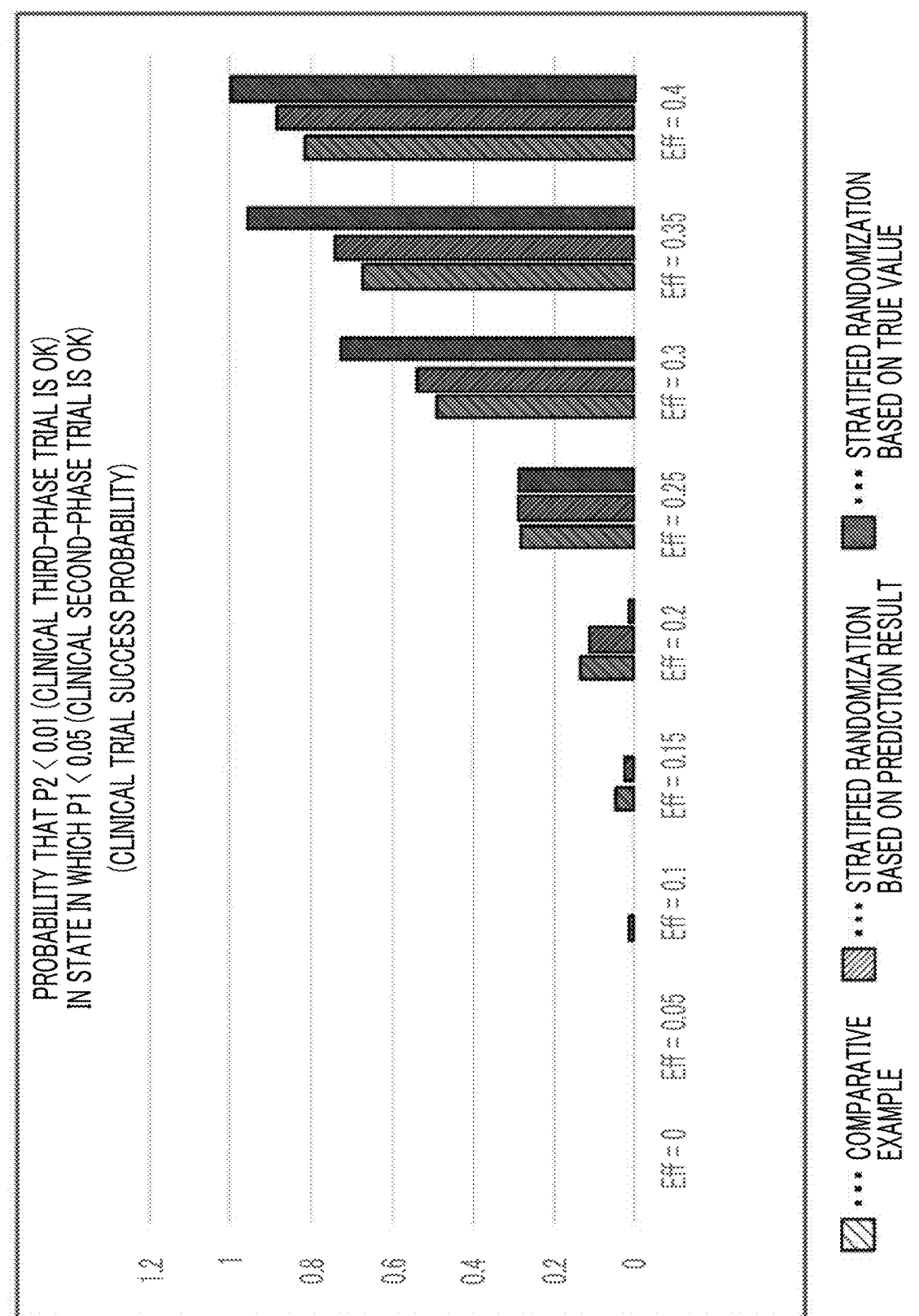
FIG. 20 is a graph showing a clinical trial success probability.

FIG. 20 shows a probability that P2<0.01 (cleared the clinical third-phase trial Ph3) in a state in which P1<0.05 (cleared the clinical second-phase trial Ph2) in a case where the efficacy Eff of the test drug was changed from 0 to 0.4 in increments of 0.05 for each of the method of the comparative example, the method according to the technology of the present disclosure in which the subjects S are randomized by stratification based on the prediction result 45, and the method of stratified randomization based on the actual CDR-SOB change amount (true value) Δc. The probability that P2<0.01 in a state in which P1<0.05 is, in other words, a clinical trial success probability.

According to FIG. 20, it can be seen that the probability that P2<0.01 in a state in which P1<0.05 in the method according to the technology of the present disclosure is mostly higher than the probability that P2<0.01 in a state in which P1<0.05 in the method of the comparative example. Therefore, according to the technology of the present disclosure, it has been confirmed that the efficacy of the test drug is legitimately evaluated and the clinical trial success probability is increased accordingly.

It is considered that the reason why the method in the related art was found to be more effective than the method according to the technology of the present disclosure in the local portions in FIGS. 19 and 20 is that there was a slight error in the prediction result 45. Therefore, it is considered that in a case where the prediction accuracy of the progression speed prediction model 31 is increased, the result shows that the method in the related art is more effective than the method according to the technology of the present disclosure.

In the present example, the example has been described in which the clinical second-phase trial Ph2 is performed in a case where the clinical first-phase trial Ph1 is cleared, and the clinical third-phase trial Ph3 is performed in a case where the clinical second-phase trial Ph2 is cleared, but the present disclosure is not limited to this. The clinical first-phase trial Ph1 and the clinical second-phase trial Ph2, or the clinical second-phase trial Ph2 and the clinical third-phase trial Ph3 may be performed in parallel.

Although the example has been described in which the encoder unit 61 of the AE 60 is used as the feature amount derivation model 51, the present disclosure is not limited to this. A part of a single task convolutional neural network or a part of a multitask convolutional neural network may be used as the feature amount derivation model 51 (see FIG. 31).

The unit of the block randomization method is not limited to the two persons given as an example. For example, the unit may be four persons. In addition, without using the block randomization method, half of the therapeutic trial subjects S who constitute the group may be simply allocated to the treatment group TG, and the remaining half may be allocated to the placebo group PG.

Second Embodiment

Figure 21:
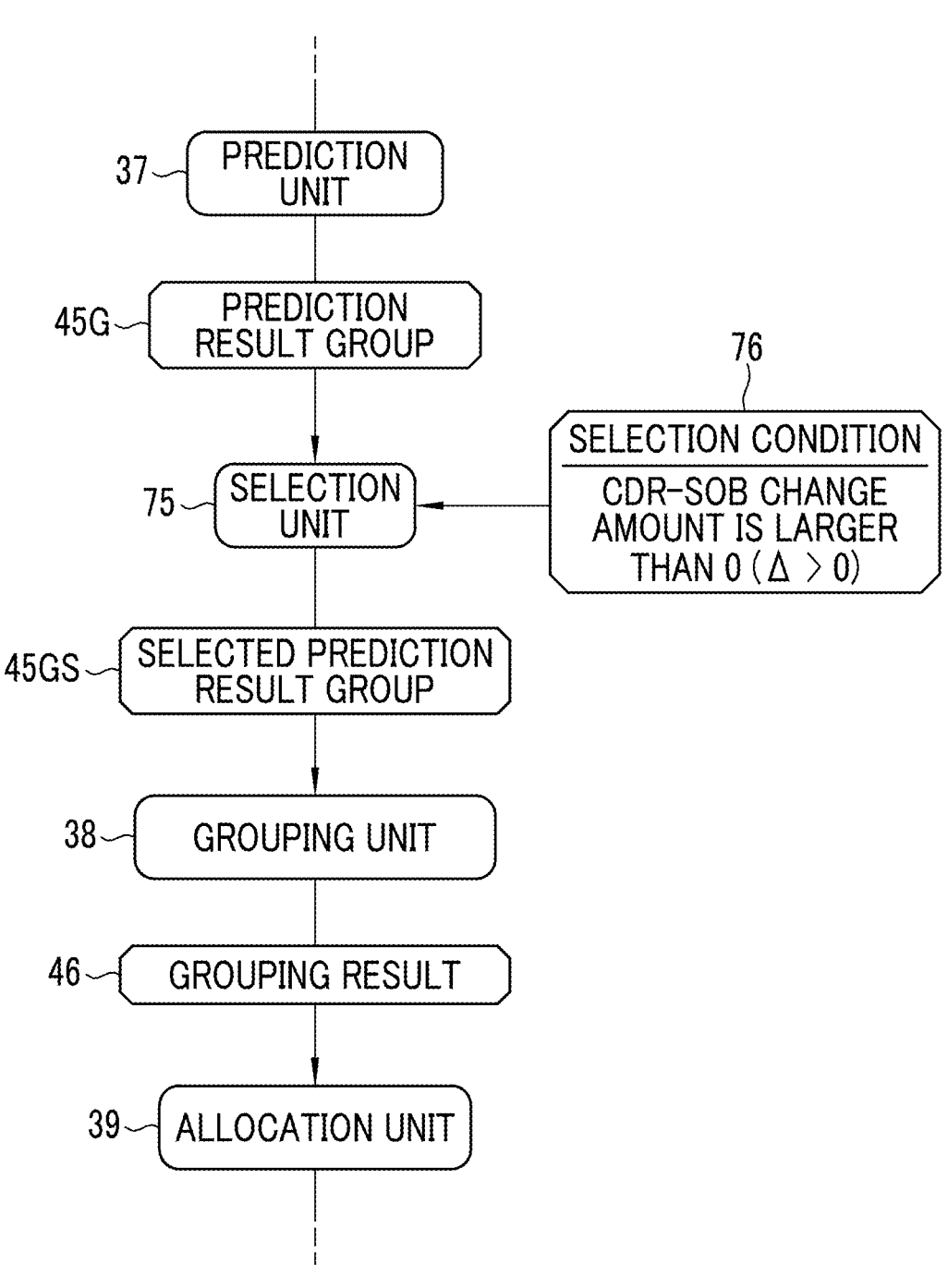
FIG. 21 is a diagram showing a processing unit of a second embodiment.

As shown in FIG. 21 as an example, the CPU of the clinical trial support server of a second embodiment functions as a selection unit 75 in addition to the processing units 35 to 40 of the first embodiment (in FIG. 21, the prediction unit 37, the grouping unit 38, and the allocation unit 39 are shown, and the others are not shown). The selection unit 75 is provided between the prediction unit 37 and the grouping unit 38. The prediction result group 45G from the prediction unit 37 is input to the selection unit 75.

The selection unit 75 selects the subject S whose progression of the dementia is relatively fast according to a selection condition 76. In the present example, the selection condition 76 is a content that the CDR-SOB change amount is larger than 0 (Δ>0). The selection unit 75 generates a selected prediction result group 45GS by selecting only the prediction result 45 satisfying the selection condition 76 from among the plurality of prediction results 45 constituting the prediction result group 45G. The selection unit 75 outputs the selected prediction result group 45GS to the grouping unit 38.

Figure 22:
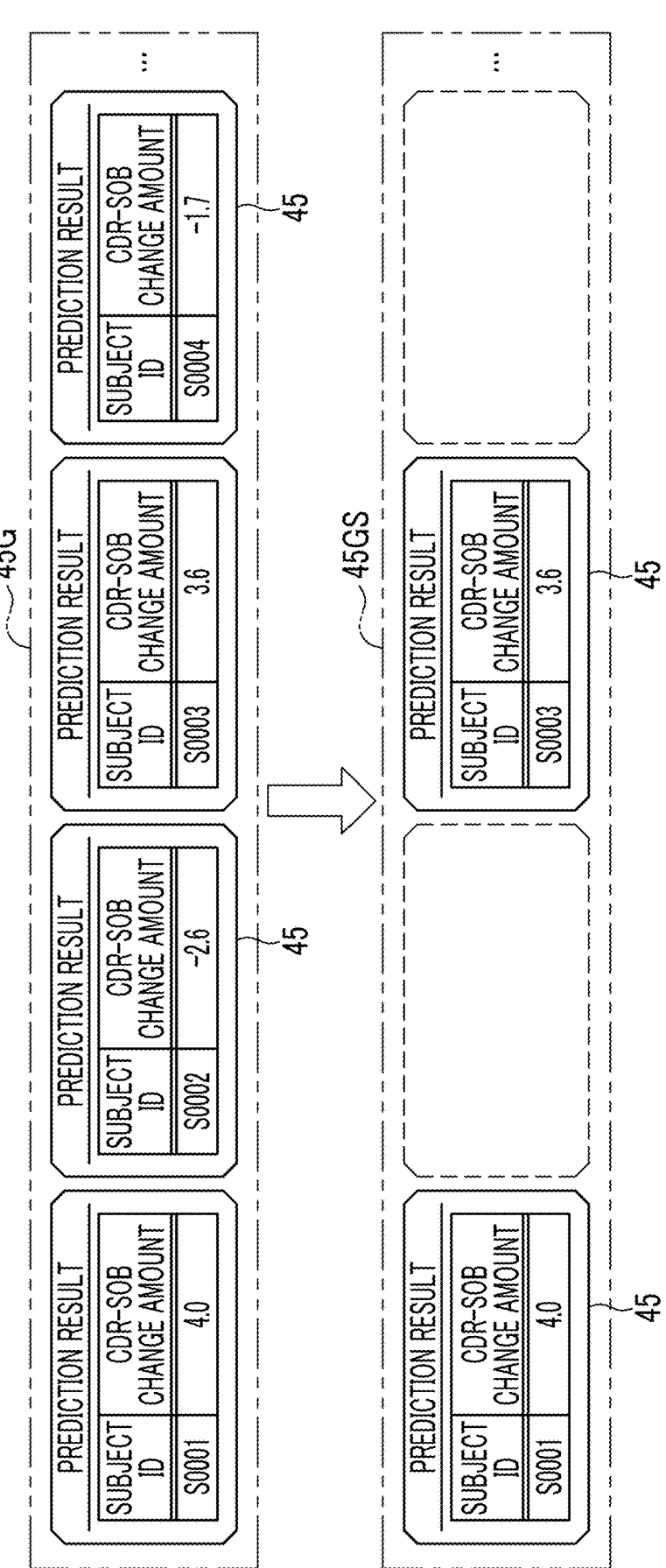
FIG. 22 is a diagram showing processing of a selection unit.

FIG. 22 shows an example of processing of the selection unit 75. In FIG. 22, the CDR-SOB change amount of the subject S whose subject ID is S0001 and S0003 is larger than 0, and the CDR-SOB change amount of the subject S whose subject ID is S0002 and S0004 is 0 or less. Therefore, the selection unit 75 generates the selected prediction result group 45GS by selecting the prediction results 45 in which the subject ID is S0001 and S0003 and excluding the prediction results 45 in which the subject ID is S0002 and S0004.

The grouping unit 38 performs grouping on the subjects S whose prediction result 45 is selected in the selected prediction result group 45GS. The allocation unit 39 allocates the subjects S whose prediction result 45 is selected in the selected prediction result group 45GS to the treatment group TG and the placebo group PG based on the grouping result 46.

As described above, in the second embodiment, the selection unit 75 selects the subject S whose progression of the dementia is relatively fast, such as the subject S whose CDR-SOB change amount is larger than 0, based on the prediction result 45. The grouping unit 38 performs the grouping according to the prediction result 45 only for the selected subjects S. In addition, the allocation unit 39 allocates only the selected subjects S to the treatment group TG and the placebo group PG. Therefore, a person who is more suitable for the clinical trial of the test drug for the dementia can be selected as the subject S, and this can further contribute to the legitimate evaluation of the efficacy of the test drug for the dementia.

The selection condition 76 is not limited to the exemplified content. For example, the content may be that the CDR-SOB change amount is larger than 2 (Δ>2). Alternatively, the content may be that the CDR-SOB change amount is larger than 0 and 3 or less (0<Δ≤3).

Third Embodiment

Figures 23, 24, 25:
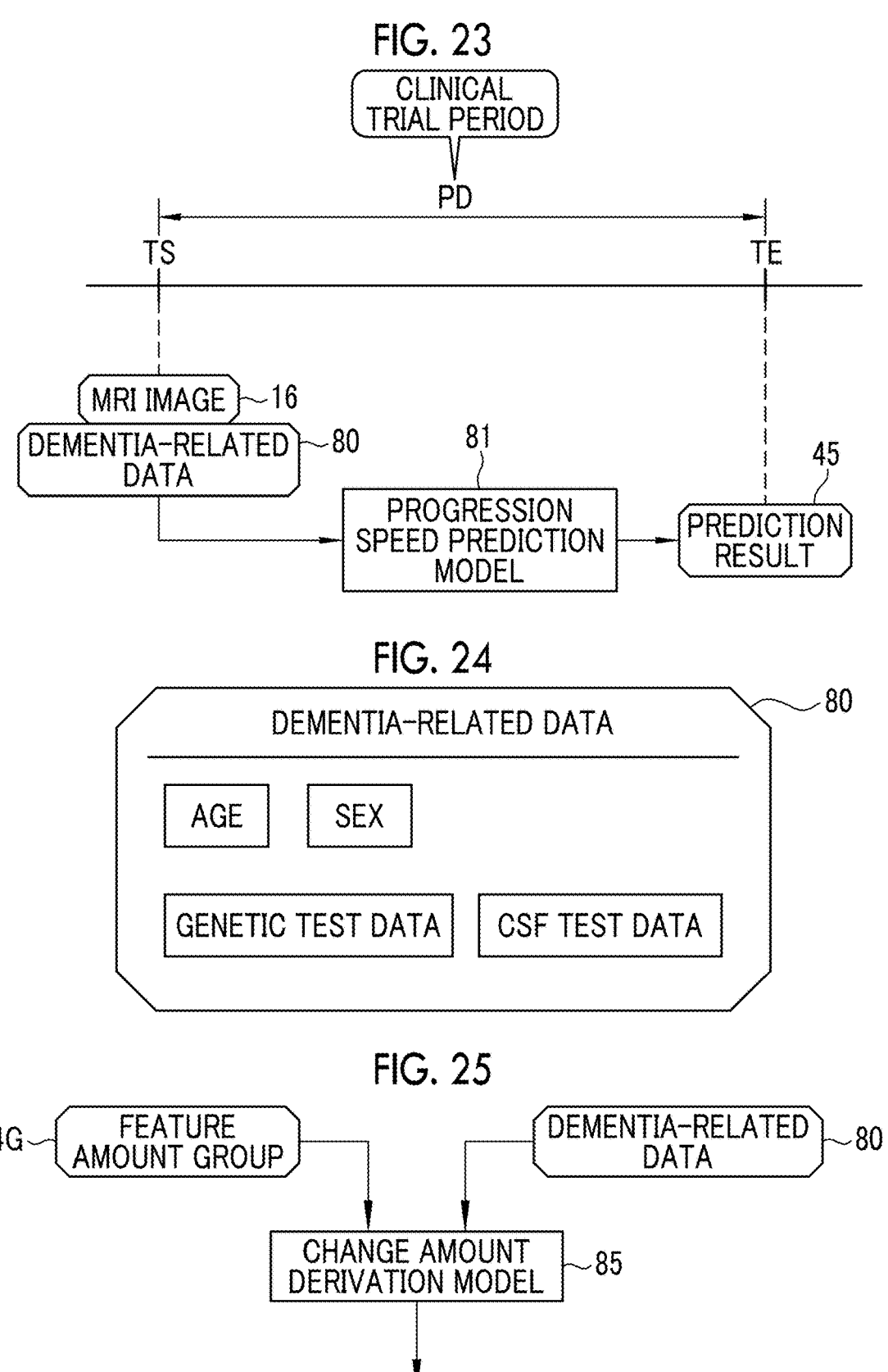
FIG. 23 is a diagram showing a third embodiment in which dementia-related data is input to a progression speed prediction model in addition to an MRI image.
FIG. 24 is a diagram showing the dementia-related data.
FIG. 25 is a diagram showing an aspect in which dementia-related data is input to a change amount derivation model in addition to a feature amount group.

As shown in FIG. 23 as an example, in a third embodiment, the prediction unit 37 inputs dementia-related data 80 to a progression speed prediction model 81 in addition to the MRI image 16. The dementia-related data 80 is data related to the dementia of the subject S at the start time point TS of the clinical trial, and includes a part of the data related to the diagnostic criteria for the dementia described above. More specifically, as shown in FIG. 24 as an example, the dementia-related data 80 includes an age, a sex, genetic test data, and CSF test data, which is blood/cerebrospinal fluid test data, of the subject S. The genetic test data is, for example, a test result of a genotype of an ApoE gene. The genotype of the ApoE gene is a combination of two types among three types of ApoE genes of ε2, ε3, and ε4 (ε2 and ε3, ε3 and ε4, and the like). A risk of developing Alzheimer's dementia in a person with a genotype including one or two of ε4 (ε2 and ε4, ε4 and ε4, and the like) is estimated to be about 3 to 12 times higher than that in a person with a genotype without ε4 (ε2 and ε3, ε3 and ε3, and the like). The CSF test data is, for example, an amount of phosphorylated tau protein (p-tau) 181 in CSF. The sex is represented by numerical values such as 00 for a male and 01 for a female. Similarly, the genetic test data is also represented by the combination of ApoE genes in a numerical form. The dementia-related data 80 is an example of "target disease-related data" according to the technology of the present disclosure.

As shown in FIG. 25 as an example, the dementia-related data 80 is input to a change amount derivation model 85 of the progression speed prediction model 81 together with the feature amount group 54G. The change amount derivation model 85 outputs the prediction result 45 by referring not only to the feature amount group 54G but also to the dementia-related data 80.

Figure 26:
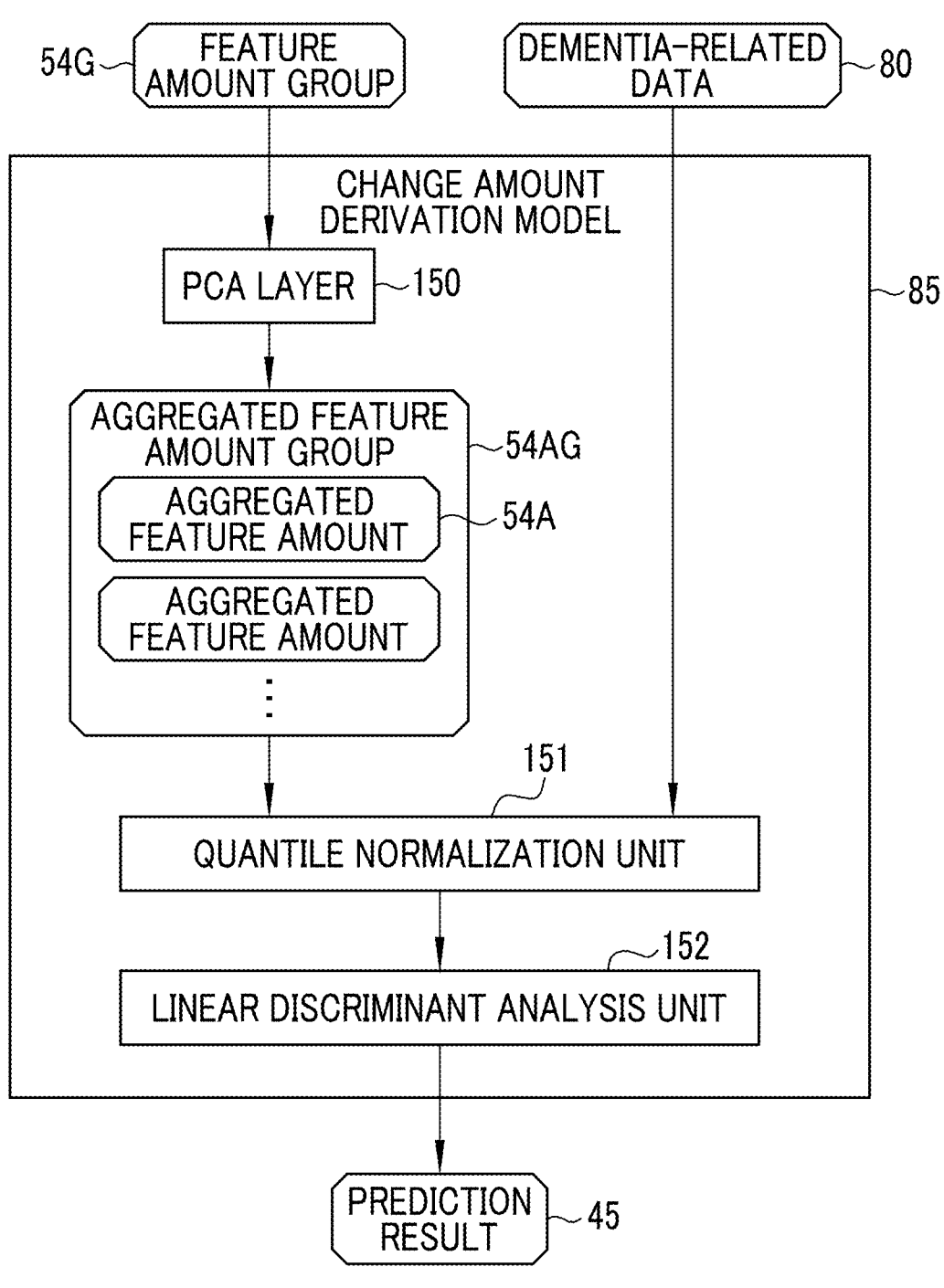
FIG. 26 is a diagram showing a detailed configuration of the change amount derivation model of the third embodiment.

As shown in FIG. 26 as an example, the change amount derivation model 85 according to the present embodiment includes a principal component analysis (hereinafter, referred to as a PCA) layer 150, a quantile normalization unit 151, and a linear discriminant analysis unit 152. The feature amount group 54G is input to the PCA layer 150. The PCA layer 150 performs PCA on each of the plurality of feature amounts 54 constituting the feature amount group 54G, and aggregates the feature amounts 54 into an aggregated feature amount 54A. For example, the PCA layer 150 aggregates several hundreds to several thousands feature amounts 54 into one aggregated feature amount 54A. The PCA layer 150 outputs an aggregated feature amount group 54AG, which is a set of the aggregated feature amounts 54A, of the respective feature amounts 54 to the quantile normalization unit 151.

The aggregated feature amount group 54AG and the dementia-related data 80 are input to the quantile normalization unit 151. In order to handle a plurality of the aggregated feature amounts 54A constituting the aggregated feature amount group 54AG and the age, the sex, the genetic test data, and the CSF test data of the subject S in the dementia-related data 80 in the same sequence, the quantile normalization unit 151 performs quantile normalization of converting these pieces of data into data that follows a normal distribution. The linear discriminant analysis unit 152 performs, for example, linear discriminant analysis using support vector regression (SVR) or the like for the aggregated feature amounts 54A and the age, the sex, the genetic test data, and the CSF test data of the subject S in the dementia-related data 80 after the quantile normalization processing, and outputs the prediction result 45 as a result.

Figure 27:
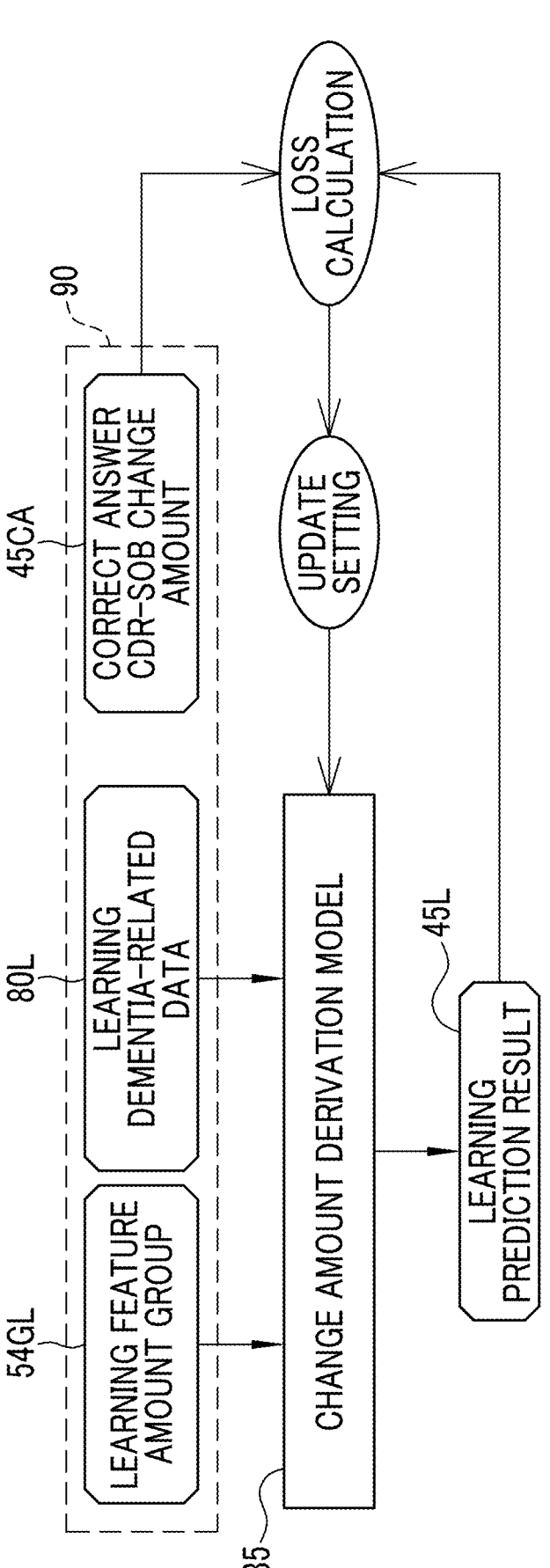
FIG. 27 is a diagram showing an outline of processing in a learning phase of the change amount derivation model of the third embodiment.

As shown in FIG. 27 as an example, the change amount derivation model 85 is trained by learning data 90. The learning data 90 is a set of the learning feature amount group 54GL, learning dementia-related data 80L, and the correct answer CDR-SOB change amount 45CA. The origins of the learning feature amount group 54GL and the correct answer CDR-SOB change amount 45CA are the same as in the learning data 70 of the first embodiment. The learning dementia-related data 80L is dementia patient's age, sex, genetic test data, and CSF test data of the learning MRI image 16L from which the learning feature amount group 54GL is obtained. The learning dementia-related data 80L is an example of "learning input data" according to the technology of the present disclosure.

In the learning phase, the learning feature amount group 54GL and the learning dementia-related data 80L are input to the change amount derivation model 85. The change amount derivation model 85 outputs the learning prediction result 45L in response to the learning feature amount group 54GL and the learning dementia-related data 80L. Loss calculation of the change amount derivation model 85 using a loss function is performed based on the learning prediction result 45L and the correct answer CDR-SOB change amount 45CA. Then, update setting of various coefficients of the change amount derivation model 85 is performed according to a result of the loss calculation, and the change amount derivation model 85 is updated according to the update setting.

In the learning phase of the change amount derivation model 85, while exchanging the learning data 90, a series of processing including inputting of the learning feature amount group 54GL and the learning dementia-related data 80L to the change amount derivation model 85, outputting of the learning prediction result 45L from the change amount derivation model 85, the loss calculation, the update setting, and updating of the change amount derivation model 85 is repeatedly performed. The repetition of the series of processing is ended in a case where prediction accuracy of the learning prediction result 45L for the correct answer CDR-SOB change amount 45CA reaches a predetermined set level. The change amount derivation model 85 in which the prediction accuracy has reached the set level in this way is used in the prediction unit 37 as a part of the progression speed prediction model 81. The learning may be ended in a case where the above-described series of processing is repeated a set number of times, regardless of the prediction accuracy of the learning prediction result 45L for the correct answer CDR-SOB change amount 45CA.

Figure 28:
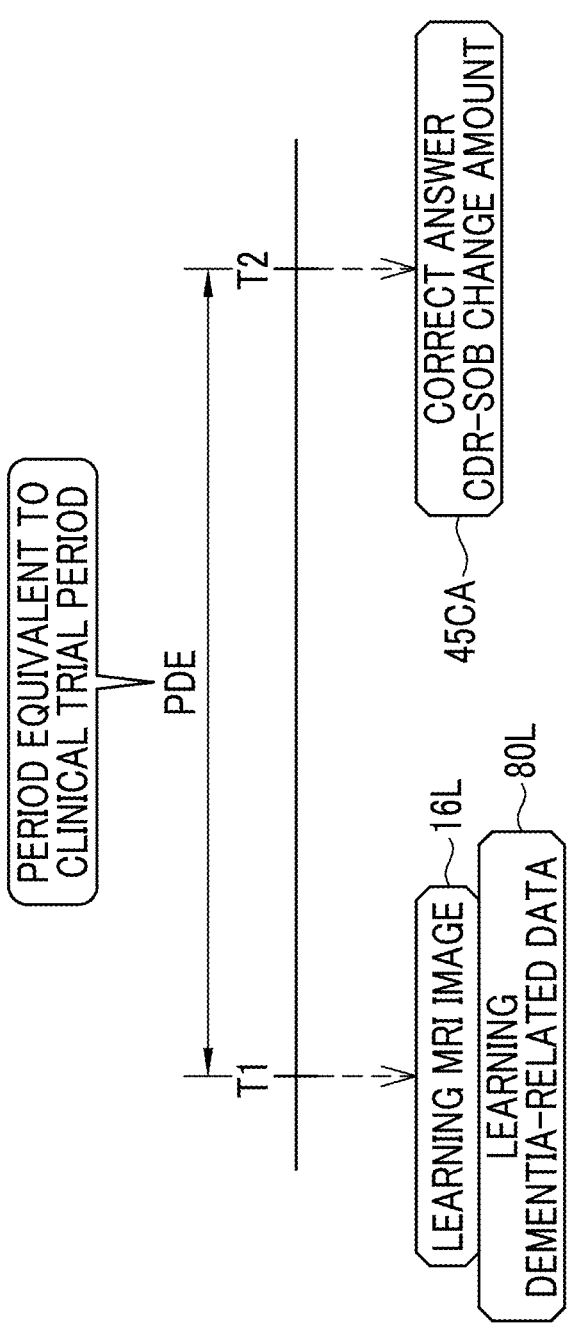
FIG. 28 is a diagram showing a time point of a learning MRI image, learning dementia-related data, and of a correct answer CDR-SOB change amount.

As shown in FIG. 28 as an example, the learning dementia-related data 80L is data related to the dementia of the dementia patient at the first time point T1, like the learning MRI image 16L.

As described above, in the third embodiment, the learning input data also includes the learning dementia-related data 80L, which is dementia-related data regarding the dementia of the dementia patient at the first time point T1. The prediction unit 37 also inputs the dementia-related data 80 regarding the dementia of the subject S at the start time point TS of the clinical trial to the progression speed prediction model 81. Since powerful data that is useful for predicting the progression speed of the dementia such as the dementia-related data 80 is added, the prediction accuracy of the progression speed of the dementia can be significantly improved as compared with a case of predicting the progression speed of the dementia only with the feature amount group 54G.

In addition to the age and the sex, the dementia-related data 80 may include a medical history, or whether or not there is a relative who has developed dementia. Results of a blood test, such as an apolipoprotein measurement value, a complement protein measurement value, and a transthyretin measurement value, may be included in the dementia-related data 80. The dementia-related data 80 may include a Hasegawa dementia scale score, an MMSE score, a rivermead behavioural memory test (RBMT) score, a score of activities of daily living (ADL), an ADAS-Cog score, and the like.

Figures 29, 30:
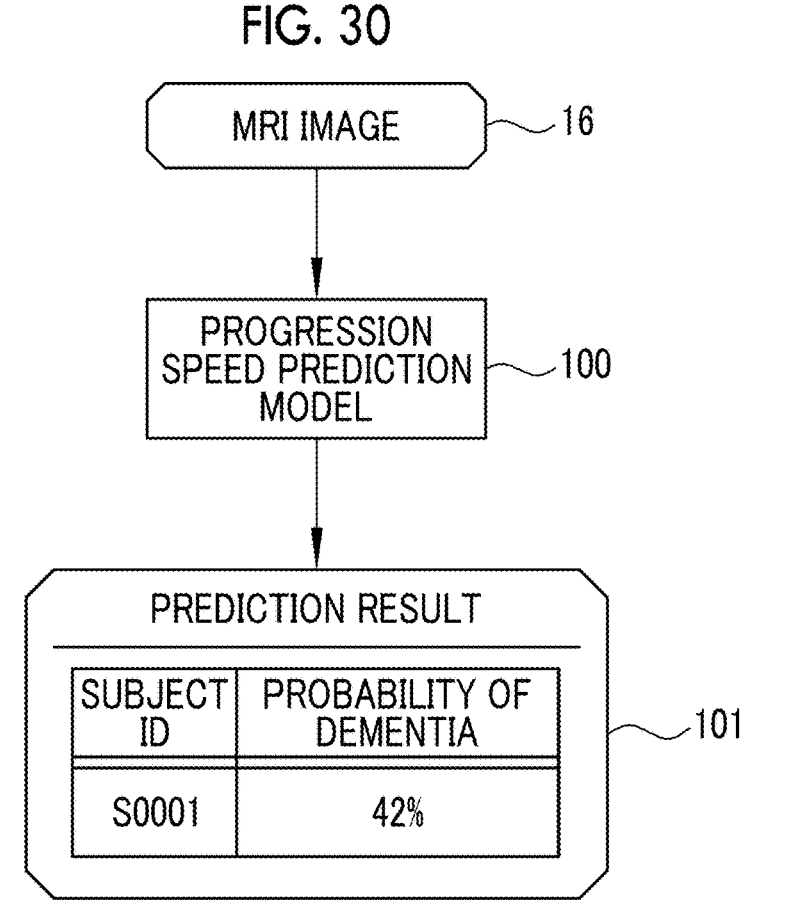
FIG. 29 is a diagram showing an aspect in which a clinical trial period is input to a progression speed prediction model in addition to an MRI image and dementia-related data.
FIG. 30 is a diagram showing an aspect in which a probability of dementia is output as a prediction result.

As shown in FIG. 29 as an example, the clinical trial period PD may be input to the progression speed prediction model 95 in addition to the MRI image 16 and the dementia-related data 80. In this case, although not shown, in the learning phase, in addition to the learning MRI image 16L and the learning dementia-related data 80L, the period PDE equivalent to the clinical trial period PD is input to the progression speed prediction model 95 as the learning input data.

In each of the above-described embodiments, the CDR-SOB change amount, which is the change amount of the score of the cognitive function test, is exemplified as the prediction result 45, but the present disclosure is not limited to this. As with a progression speed prediction model 100 shown in FIG. 30 as an example, a probability of the dementia may be output as the prediction result 101. In this case, the grouping may be performed into, for example, a group 1 in which the probability of the dementia is 0% or more and less than 25%, a group 2 in which the probability of the dementia is 25% or more and less than 50%, a group 3 in which the probability of the dementia is 50% or more and less than 75%, and a group 4 in which the probability of the dementia is 75% or more and 100% or less.

As an example, a part of a multitask convolutional neural network (hereinafter, referred to as a multitask CNN) 200 shown in FIG. 31 may be used as the feature amount derivation model 51.

Figure 31:
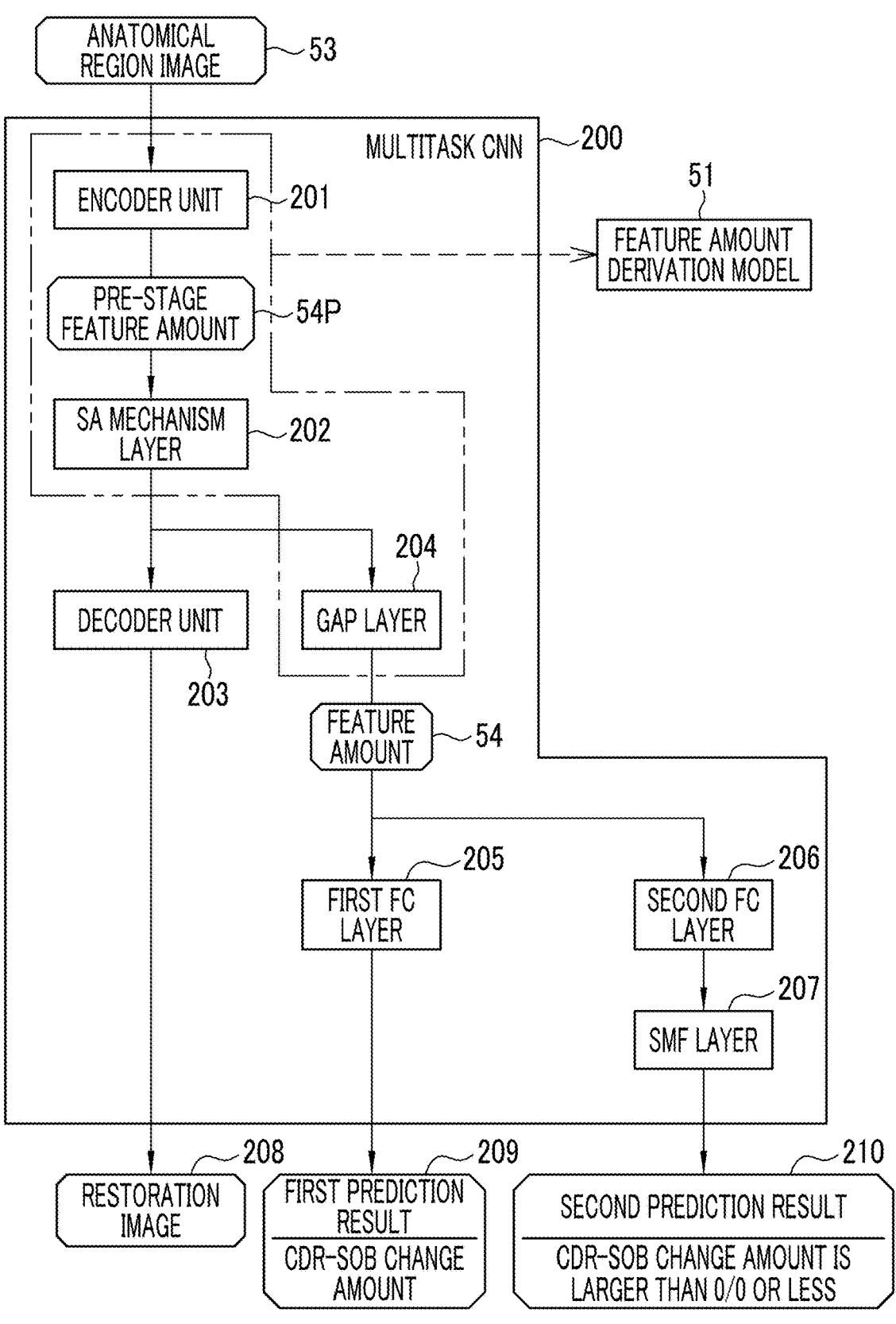
FIG. 31 is a diagram showing a configuration of a multitask CNN and a structure of a feature amount derivation model.

In FIG. 31, the multitask CNN 200 includes an encoder unit 201, a self-attention (hereinafter, referred to as SA) mechanism layer 202, a decoder unit 203, a global average pooling (hereinafter, referred to as GAP) layer 204, a first fully connected (hereinafter, referred to as FC) layer 205, a second FC layer 206, and a softmax function (hereinafter, referred to as SMF) layer 207.

The encoder unit 201 converts the input anatomical region image 53 into a pre-stage feature amount 54P, as with the encoder unit 61 of the AE 60 of the first embodiment. The encoder unit 201 outputs the pre-stage feature amount 54P to the SA mechanism layer 202.

The SA mechanism layer 202 performs convolution operation while changing a coefficient of a filter for the convolution operation in accordance with a value of an element which is a target of the convolution operation, on the pre-stage feature amount 54P. The SA mechanism layer 202 outputs the pre-stage feature amount 54P after the convolution operation, to the decoder unit 203 and the GAP layer 204.

The decoder unit 203 generates a restoration image 208 of the anatomical region image 53 from the pre-stage feature amount 54P after the convolution operation, as with the decoder unit 62 of the AE 60 of the first embodiment.

The GAP layer 204 performs the global average pooling processing on the pre-stage feature amount 54P after the convolution operation. The global average pooling processing is processing of obtaining an average value for each of a plurality of channels of the pre-stage feature amount 54P. For example, in a case where the number of channels of the pre-stage feature amount 54P is 512, an average value of 512 pre-stage feature amounts 54P is obtained by the global average pooling processing. The GAP layer 204 outputs the obtained average value of the pre-stage feature amounts 54P as the feature amount 54 to the first FC layer 205 and the second FC layer 206.

The first FC layer 205 outputs a first prediction result 209 based on the feature amount 54. The first prediction result 209 is the CDR-SOB change amount, as with the prediction result 45. The first FC layer 205 has an input layer having units corresponding to the number of the feature amounts 54 and one output layer for outputting the first prediction result 209. Each unit of the input layer and the output layer are fully connected to each other, and a weight is set for each. The feature amount 54 is input to each unit of the input layer. A product sum of the feature amount 54 and the weight set for each unit is an output value of the output layer. This output value is the CDR-SOB change amount.

The second FC layer 206 converts the feature amount 54 into a variable handled by the SMF of the SMF layer 207. The second FC layer 206 has an input layer having units corresponding to the number of the feature amounts 54 and an output layer having units corresponding to the number of the variables handled by the SMF. Each unit of the input layer and each unit of the output layer are fully connected to each other, and a weight is set for each unit. The feature amount 54 is input to each unit of the input layer. A product sum of the feature amount 54 and the weight set for each unit is an output value of each unit of the output layer. This output value is a variable handled by the SMF. The second FC layer 206 outputs the variable handled by the SMF to the SMF layer 207. The SMF layer 207 outputs a second prediction result 210 by applying the variable to the SMF. A content of the second prediction result 210 is such that the CDR-SOB change amount is larger than 0 or 0 or less.

That is, the multitask CNN 200 performs three tasks of the AE, the prediction of the continuous quantity (CDR-SOB change amount), and the class classification (whether the CDR-SOB change amount is larger than 0 or 0 or less). In the feature amount derivation model 51, the encoder unit 201, the SA mechanism layer 202, and the GAP layer 204 are used as the parts.

As described above, a part of the multitask CNN 200 may be used as the feature amount derivation model 51. The multitask CNN 200 performs more complex processing in order to perform a plurality of tasks compared to the AE 60 or the like. Therefore, the feature amount 54 output from a part of the multitask CNN 200 is likely to more comprehensively represent the feature of the anatomical region image 53. Therefore, in a case where a part of the multitask CNN 200 is used as the feature amount derivation model 51, the prediction result 45 based on the feature amount 54 having higher reliability is output, so that the accuracy of the prediction of the progression speed of the dementia can be further improved.

The progression speed of dementia of the subject S may be predicted by using the regression model disclosed in <S. Ostrowitzki, et al: A phase III randomized trial of gantenerumab in prodromal Alzheimer's disease, Alzheimer's Research & Therapy, 2017.>.

The medical image is not limited to the illustrated MRI image 16. The medical image may be a PET image or a SPECT image.

The learning of the AE 60 shown in FIG. 9, the learning of the change amount derivation model 52 shown in FIG. 10, and the learning of the change amount derivation model 85 shown in FIG. 27 may be performed in the clinical trial support server 10, or may be performed in an apparatus different from the clinical trial support server 10. In addition, these kinds of learning may be continued after the models are stored in the storage 20 of the clinical trial support server 10.

The clinical trial support server 10 may be installed in each drug development facility, or may be installed in a data center independent of the drug development facility. In addition, the operator terminal 11 may perform a part or all of the functions of each processing unit of the clinical trial support server 10.

Although dementia has been exemplified as the target disease, the present disclosure is not limited to this. The target disease may be, for example, cerebral infarction. In this case, a CT image or an MRI image showing the brain of the subject is input to the trained model, and a change amount of a National Institutes of Health Stroke Scale (NIHSS) score or a change amount of a Japan Stroke Scale (JSS) score is output from the trained model. The target disease is preferably a cranial nerve disease including a neurodegenerative disease and a cerebrovascular disease such as the exemplified dementia and cerebral infarction, or Parkinson's disease.

Note that the dementia has become a social problem with the advent of an aging society in recent years. Therefore, the present example in which the target disease is dementia can be said to be a form that matches the current social problem.

The target disease is not limited to the cranial nerve disease, and thus the organ is not limited to the brain.

The progression speed of the target disease of the subject S may be predicted without using the trained model such as the progression speed prediction model 31.

In each of the above-described embodiments, for example, as a hardware structure of a processing unit that executes various types of processing, such as the reception unit 35, the RW control unit 36, the prediction unit 37, the grouping unit 38, the allocation unit 39, the distribution control unit 40, and the selection unit 75, various processors shown below can be used. As described above, the various processors include, in addition to the CPU 22 that is a general-purpose processor which executes software (operation program 30) to function as various processing units, a programmable logic device (PLD) that is a processor of which a circuit configuration can be changed after manufacture, such as a field programmable gate array (FPGA), and a dedicated electrical circuit that is a processor having a circuit configuration which is designed for exclusive use to execute specific processing, such as an application specific integrated circuit (ASIC).

One processing unit may be configured of one of the various processors or may be configured of a combination of two or more processors of the same type or different types (for example, a combination of a plurality of FPGAs and/or a combination of a CPU and an FPGA). In addition, a plurality of processing units may be configured of one processor.

As an example of configuring the plurality of processing units with one processor, first, there is a form in which, as typified by computers such as a client and a server, one processor is configured of a combination of one or more CPUs and software and the processor functions as the plurality of processing units. Second, there is a form in which, as typified by a system on chip (SoC) and the like, a processor that implements functions of an entire system including the plurality of processing units with one integrated circuit (IC) chip is used. As described above, the various processing units are configured using one or more of the various processors as a hardware structure.

In addition, more specifically, an electric circuit (circuitry) in which circuit elements, such as semiconductor elements, are combined can be used as the hardware structure of these various processors.

It is possible to understand the techniques described in following Appendices from the above description.

Appendix 1

A clinical trial support apparatus comprising: a processor, in which the processor predicts a progression speed of a target disease for subjects of a clinical trial, divides the subjects into a plurality of groups according to a prediction result of the progression speed of the target disease, and allocates the subjects to a treatment group to which a test drug is administered and a placebo group to which a placebo is administered for each of the plurality of groups.

Appendix 2

The clinical trial support apparatus according to Appendix 1, in which the processor selects subjects whose progression of the target disease is relatively fast based on the prediction result, and performs grouping according to the prediction result and allocation to the treatment group and the placebo group, only for the selected subjects.

Appendix 3

The clinical trial support apparatus according to Appendix 1 or 2, in which the processor allocates the subjects to the treatment group and the placebo group by using a block randomization method.

Appendix 4

The clinical trial support apparatus according to any one of Appendices 1 to 3, in which the processor predicts the progression speed of the target disease by using a trained model, the trained model is a trained model that has been trained by using a medical image showing an organ of a target disease patient at a first time point as learning input data and a numerical value indicating a degree of progression of the target disease of the target disease patient at a second time point after a lapse of a period equivalent to a clinical trial period from the first time point as correct answer data, and the processor inputs a medical image showing an organ of the subject at a start time point of the clinical trial to the trained model, and outputs a numerical value indicating a degree of progression of the target disease of the subject at an end time point of the clinical trial as the prediction result from the trained model.

Appendix 5

The clinical trial support apparatus according to Appendix 4, in which, via the trained model, a plurality of anatomical region images, which are images of a plurality of anatomical regions of the organ, are extracted from the medical image at the start time point of the clinical trial, and the anatomical region image is input to a feature amount derivation model prepared for each of the anatomical regions, and a feature amount of the anatomical region is output from the feature amount derivation model.

Appendix 6

The clinical trial support apparatus according to Appendix 4 or 5, in which the learning input data also includes target disease-related data regarding the target disease of the target disease patient at the first time point, and the processor also inputs target disease-related data regarding the target disease of the subject at the start time point of the clinical trial to the trained model.

Appendix 7

The clinical trial support apparatus according to any one of Appendices 4 to 6, in which the target disease is dementia, and the numerical value is a change amount of a score of a cognitive function test or a probability of the dementia.

Appendix 8

The clinical trial support apparatus according to any one of Appendices 1 to 7, in which the target disease is a cranial nerve disease.

Appendix 9

The clinical trial support apparatus according to any one of Appendices 1 to 8, in which the target disease is dementia.

In the technology of the present disclosure, the above-described various embodiments and/or various modification examples may be combined with each other as appropriate. In addition, it is needless to say that the present disclosure is not limited to each of the above-described embodiments, and various configurations can be used without departing from the gist of the present disclosure. Further, the technology of the present disclosure extends to a storage medium that non-transitorily stores a program in addition to the program.

The above descriptions and illustrations are detailed descriptions of portions related to the technology of the present disclosure and are merely examples of the technology of the present disclosure. For example, description related to the above configurations, functions, actions, and effects is description related to an example of configurations, functions, actions, and effects of the parts according to the embodiment of the disclosed technology. Therefore, unnecessary portions may be deleted or new elements may be added or replaced in the above descriptions and illustrations without departing from the gist of the technology of the present disclosure. Further, in order to avoid complications and facilitate understanding of the parts related to the technology of the present disclosure, descriptions of common general knowledge and the like that do not require special descriptions for enabling the implementation of the technology of the present disclosure are omitted, in the contents described and shown above.

In the present specification, the term "A and/or B" is synonymous with the term "at least one of A or B". That is, the term "A and/or B" means only A, only B, or a combination of A and B. In addition, in the present specification, the same approach as "A and/or B" is applied to a case in which three or more matters are represented by connecting the matters with "and/or".

All documents, patent applications, and technical standards mentioned in the present specification are incorporated herein by reference to the same extent as in a case in which each document, each patent application, and each technical standard are specifically and individually described by being incorporated by reference.

What is claimed is:

1. A clinical trial support apparatus comprising:
a processor,
wherein the processor
predicts a progression speed of a target disease for subjects of a clinical trial,
divides the subjects into a plurality of groups according to a prediction result of the progression speed of the target disease, and
allocates the subjects to a treatment group to which a test drug is administered and a placebo group to which a placebo is administered for each of the plurality of groups,
wherein the processor predicts the progression speed of the target disease by using a trained model, the trained model is a trained model that has been trained by using a medical image showing an organ of a target disease patient at a first time point as learning input data and a numerical value indicating a degree of progression of the target disease of the target disease patient at a second time point after a lapse of a period equivalent to a clinical trial period from the first time point as correct answer data, and
the processor
inputs a medical image showing an organ of the subject at a start time point of the clinical trial to the trained model, and
outputs a numerical value indicating a degree of progression of the target disease of the subject at an end time point of the clinical trial as the prediction result from the trained model.

2. The clinical trial support apparatus according to claim 1,
wherein the processor
selects subjects whose progression of the target disease is relatively fast based on the prediction result, and
performs grouping according to the prediction result and allocation to the treatment group and the placebo group, only for the selected subjects.

3. The clinical trial support apparatus according to claim 1,
wherein the processor allocates the subjects to the treatment group and the placebo group by using a block randomization method.

4. The clinical trial support apparatus according to claim 1,
wherein, via the trained model,
a plurality of anatomical region images, which are images of a plurality of anatomical regions of the organ, are extracted from the medical image at the start time point of the clinical trial, and
the anatomical region image is input to a feature amount derivation model prepared for each of the anatomical regions, and a feature amount of the anatomical region is output from the feature amount derivation model.

5. The clinical trial support apparatus according to claim 1,
wherein the learning input data also includes target disease-related data regarding the target disease of the target disease patient at the first time point, and
the processor also inputs target disease-related data regarding the target disease of the subject at the start time point of the clinical trial to the trained model.

6. The clinical trial support apparatus according to claim 1,
wherein the target disease is dementia, and
the numerical value is a change amount of a score of a cognitive function test or a probability of the dementia.

7. The clinical trial support apparatus according to claim 1,
wherein the target disease is a cranial nerve disease.

8. The clinical trial support apparatus according to claim 1,
wherein the target disease is dementia.

9. An operation method of a clinical trial support apparatus, the method comprising:
predicting a progression speed of a target disease for subjects of a clinical trial;
dividing the subjects into a plurality of groups according to a prediction result of the progression speed of the target disease; and allocating the subjects to a treatment group to which a test drug is administered and a placebo group to which a placebo is administered for each of the plurality of groups, wherein a processor predicts the progression speed of the target disease by using a trained model, the trained model is a trained model that has been trained by using a medical image showing an organ of a target disease patient at a first time point as learning input data and a numerical value indicating a degree of progression of the target disease of the target disease patient at a second time point after a lapse of a period equivalent to a clinical trial period from the first time point as correct answer data, and the processor inputs a medical image showing an organ of the subject at a start time point of the clinical trial to the trained model, and outputs a numerical value indicating a degree of progression of the target disease of the subject at an end time point of the clinical trial as the prediction result from the trained model.

10. A non-transitory computer-readable storage medium storing an operation program of a clinical trial support apparatus, the program causing a computer to execute:

predicting a progression speed of a target disease for subjects of a clinical trial;

dividing the subjects into a plurality of groups according to a prediction result of the progression speed of the target disease; and allocating the subjects to a treatment group to which a test drug is administered and a placebo group to which a placebo is administered for each of the plurality of groups, wherein the predicting the progression speed of the target disease is performed using a trained model, the trained model is a trained model that has been trained by using a medical image showing an organ of a target disease patient at a first time point as learning input data and a numerical value indicating a degree of progression of the target disease of the target disease patient at a second time point after a lapse of a period equivalent to a clinical trial period from the first time point as correct answer data, a medical image showing an organ of the subject at a start time point of the clinical trial is inputted to the trained model, and a numerical value indicating a degree of progression of the target disease of the subject at an end time point of the clinical trial as the prediction result is outputted from the trained model.

* * * * *